United States Patent
Kimura et al.

(10) Patent No.: US 8,361,345 B2
(45) Date of Patent: Jan. 29, 2013

(54) COMPOUND, POLYMERIZABLE LIQUID CRYSTAL COMPOSITION, POLYMER AND FILM

(75) Inventors: Masaomi Kimura, Kanagawa (JP);
Shunya Katoh, Kanagawa (JP);
Mitsuyoshi Ichihashi, Kanagawa (JP);
Yasuhiro Ishiwata, Kanagawa (JP);
Masatoshi Mizumura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 129 days.

(21) Appl. No.: 13/073,520

(22) Filed: Mar. 28, 2011

(65) Prior Publication Data

US 2011/0233465 A1    Sep. 29, 2011

(30) Foreign Application Priority Data

Mar. 29, 2010 (JP) .................. 2010-074760

(51) Int. Cl.
*C09K 19/38* (2006.01)
*C09K 19/20* (2006.01)
*C07C 255/41* (2006.01)
*C07C 327/28* (2006.01)
*C07C 327/32* (2006.01)
*C08F 20/30* (2006.01)
*C08F 22/26* (2006.01)
*C08F 22/30* (2006.01)
*C08L 35/04* (2006.01)
*G02B 5/30* (2006.01)

(52) U.S. Cl. .................. 252/299.67; 558/257; 558/400; 526/286; 526/298

(58) Field of Classification Search ............. 252/299.01, 252/299.67; 558/257, 400; 526/286, 296
See application file for complete search history.

(56) References Cited

U.S. PATENT DOCUMENTS

| | | | |
|---|---|---|---|
| 6,613,246 B2 * | 9/2003 | Takeuchi et al. ......... | 252/299.67 |
| 2005/0227021 A1 | 10/2005 | Harding et al. | |

FOREIGN PATENT DOCUMENTS

| | | | |
|---|---|---|---|
| GB | 2 306 470 A | | 5/1997 |
| JP | 2005-120091 A | | 5/2005 |
| JP | 2005148118 A | * | 6/2005 |
| JP | 2009-149754 A | | 7/2009 |
| WO | WO 2004/090025 A1 | | 10/2004 |
| WO | WO 2005/014756 A1 | | 2/2005 |
| WO | WO 2006/010431 A1 | | 2/2006 |

OTHER PUBLICATIONS

CAPLUS 2005: 492863, 2005.*
Broer et al., "Photo-Induced Diffusion in Polymerizing Chiral-Nematic Media", Advanced Materials, 1999, vol. 11, No. 7, pp. 573-578.

* cited by examiner

*Primary Examiner* — Shean C Wu
(74) *Attorney, Agent, or Firm* — Birch, Stewart, Kolasch & Birch, LLP

(57) ABSTRACT

A compound represented by formula (I) is disclosed. $P^1$ and $P^2$ represent a polymerizable group; m1 and m2 represent an integer of from 1 to 10, "A" represents a divalent group having a 5- to 18-membered aromatic hydrocarbon ring or a 5- to 18-membered aromatic hetero ring, $L^3$ and $L^4$ represent a $C_{1-10}$ alkyl group or a $C_{1-10}$ alkoxy group, k1 and k2 represent an integer of from 0 to 4, $X^1$, $X^2$, $X^3$ and $X^4$ represent —O—, —S—, —NH—, —NR— or —SiR°R°°—, n1 and n2 represent 0 or 1, provided that at least one of them is 1; and $L^{1a}$, $L^{1b}$, $L^{2a}$ and $L^{2b}$ represent a hydrogen atom, halogen atom, —CN, —NC, —NCO, —NCS, or —OCN, provided that those in which both of $X^2$ and $X^3$ represent —O—, those in which one of $X^2$ and $X^3$ represents —O— and another represents —NH— or —NR— are excluded only when n1 is 1, both of $L^{1a}$ and $L^{1b}$ are hydrogen atoms, n2 is 1, and both of $L^{2a}$ and $L^{2b}$ are hydrogen atoms, or only when n1 is 1, both of $L^{1a}$ and $L^{1b}$ are hydrogen atoms, and n2 is 0.

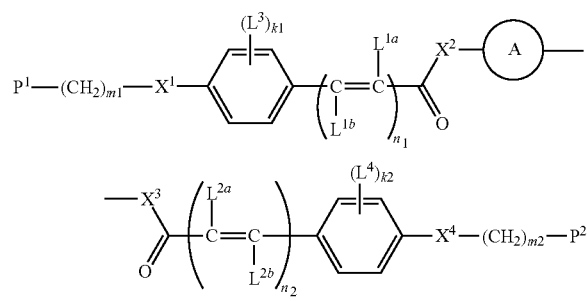

14 Claims, No Drawings

COMPOUND, POLYMERIZABLE LIQUID CRYSTAL COMPOSITION, POLYMER AND FILM

CROSS-REFERENCE TO RELATED APPLICATIONS

The present application claims the benefit of priority from Japanese Patent Application No. 2010-074760, filed on Mar. 29, 2010, the contents of which are herein incorporated by reference in their entirety.

BACKGROUND OF THE INVENTION

1. Field of the Invention

The present invention relates to a polymerizable liquid crystal compound, polymerizable liquid crystal composition and polymer useful in various applications such as optical members of which examples include optically anisotropic films and heat-shielding films, and also relates to films employing these.

2. Background Art

Recently, the demands for liquid crystal displaying devices, having a smaller size, are more and more increased; and in accordance with increasing of the demands, the demands for optical films, having a thinner thickness, also are more and more increased. For example, using liquid crystal having high Δn for preparing optical films such as retardation films may contribute to making the thickness thereof thin. Δn is one of the important properties of a liquid crystal compound; and a liquid crystal compound, having high Δn, is useful in various technical fields of optical elements such as retardation plates, polarizing elements, selective reflection films, color filters, anti-reflection films, optical compensation films, holography, and alignment layers (D. J. Broer, G. N. Mol, J. A. M. M. Van Haaren, and J. LubAdv. Mater., 1999, 11, 573).

Previously, various compounds having a cinnamate group have been proposed as a polymerizable liquid crystal compound (JP-A-2005-120091, JP-A-2009-149754, WO2006/010431, WO2005/014756, WO2004/090025 and GB 2306470).

SUMMARY OF THE INVENTION

However, the Δn values of the known polymerizable liquid crystal compounds may not be sufficient, and transparency, solubility or coating-properties thereof may not be also sufficient, which may suffer from poor film-forming properties. The known polymerizable liquid crystal compounds may not be sufficient in terms of alignment and polymerization abilities, which may result in poor optical characteristics of the cured films or in causing scattering in the films.

One object of the invention is to provide a novel polymerizable compound showing high Δn and good compatibility with another liquid crystal material or solubility in solvent.

Another object of the invention is to provide a polymerizable liquid crystal composition and polymer, employing the polymerizable liquid crystal compound, useful in various applications Another object of the invention is to provide a film, employing the polymerizable compound, useful in various applications The means for achieving the objects are as follows.

[1] A compound represented by formula (I):

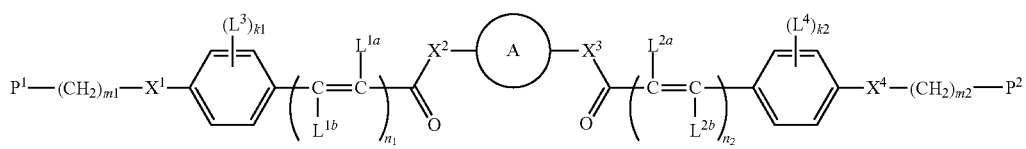

where $P^1$ and $P^2$ each independently represent a polymerizable group;

m1 and m2 each independently represent an integer of from 1 to 10, and one $CH_2$ or two or more $CH_2$, which may be not adjacent to each other, in $—(CH_2)_{m1}—$ and $—(CH_2)_{m2}—$ may be replaced with —O— or —S—;

"A" represents a divalent group having a 5- to 18-membered aromatic hydrocarbon ring or a 5- to 18-membered aromatic hetero ring, in which at least one hydrogen atom may be replaced with a $C_{1-4}$ alkyl group, $C_{1-4}$ alkoxy group or halogen atom;

$L^3$ and $L^4$ each independently represent a $C_{1-10}$ alkyl group or a $C_{1-10}$ alkoxy group, k1 and k2 each independently represent an integer of from 0 to 4;

$X^1$, $X^2$, $X^3$ and $X^4$ each independently represent —O—, —S—, —NH—, —NR— or $—SiR^OR^{OO}—$, R, $R^O$ and $R^{OO}$ each independently represent a $C_{1-10}$ alkyl group;

n1 and n2 each independently represent 0 or 1, provided that at least one of them is 1; and $L^{1a}$, $L^{1b}$, $L_{2a}$ and $L^{2b}$ each independently represent a hydrogen atom, halogen atom, —CN, —NC, —NCO, —NCS, or —OCN, provided that those in which both of $X^2$ and $X^3$ represent —O—, those in which one of $X^2$ and $X^3$ represents —O— and another represents —NH— or —NR— are excluded only when n1 is 1, both of $L^{1a}$ and $L^{1b}$ are hydrogen atoms, n2 is 1, and both of $L^{2a}$ and $L^{2b}$ are hydrogen atoms, or only when n1 is 1, both of $L^{1a}$ and $L^{1b}$ are hydrogen atoms, and n2 is 0.

[2] The compound of [1], wherein "A" is a divalent group having a 6-membered aromatic hydrocarbon ring.

[3] The compound of [1] or [2], wherein at least one of $X^2$ and $X^3$ represents —S—.

[4] The compound of any one of [1]-[3], wherein $P^1$ and $P^2$ each independently represent a polymerizable group selected from the group consisting of the groups represented by (P-1)-(P-5) shown below:

(P-1)

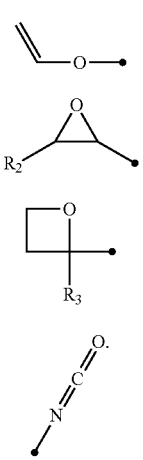

(P-2)

(P-3)

(P-4)

(P-5)

where $R^1$ to $R^3$ each independently represent a hydrogen atom or methyl.

[5] The compound of any one of [1]-[4], wherein $P^1$ and $P^2$ each independently represent a methacrylate or acrylate group.

[6] A polymerizable liquid crystal composition comprising at least one compound of any one of [1]-[5].

[7] The polymerizable liquid crystal composition of [6], comprising at least one chiral compound.

[8] A polymer prepared by polymerizing a compound of any one of [1]-[5], or prepared by polymerizing a polymerizable liquid crystal composition of [6] or [7].

[9] A film comprising at least one polymer of [8].

[10] A film formed by curing a cholesteric liquid crystal phase of a polymerizable liquid crystal composition of [7].

[11] The film of [9] or [10], having optical anisotropy.

[12] The film of any one of [9]-[11], having selective reflection.

[13] The film of [12], having selective reflection in the infrared region.

According to the invention, it is possible to provide a novel polymerizable liquid crystal compound showing high Δn and good compatibility with another liquid crystal material or solubility in a solvent.

According to the invention, it is to provide a polymerizable liquid crystal composition and polymer, employing the polymerizable liquid crystal compound, useful in various applications.

According to the invention, it is possible to provide a film, employing the polymerizable liquid crystal compound, useful in various applications.

DETAILED DESCRIPTION OF THE INVENTION

The present invention will be detailed below. In this description, the numerical range expressed by the wording "a number to another number" means the range that falls between the former number indicating the lowermost limit of the range and the latter number indicating the uppermost limit thereof.

1. Polymerizable Liquid Crystal Compound

The present invention relates to a polymerizable compound represented by formula (I). One feature of the compound of the invention resides in having at least one cinnamate group. The compound of the invention shows higher Δn compared with the known compound having a cinnamate group. The compound of the invention shows also good compatibility with another liquid crystal material or solubility in a solvent, is polymerizable, and is useful in various applications such as optical members.

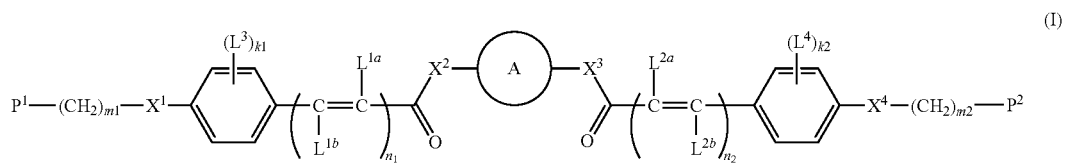

(I)

In the formula, $P^1$ and $P^2$ each independently represent a polymerizable group. Examples of the polymerizable group include any functional groups capable of carrying out radical polymerization or cationic polymerization. The radical polymerizable group is not limited and may be selected from any known radical polymerizable groups. Preferable examples of the radical polymerizable group include (meth)acrylates (used as a meaning indicating both of acrylate and methacrylate). The cationic polymerizable group is not limited and may be selected from any known cationic polymerizable groups. Examples of the cationic polymerizable group include an alicyclic ether group, cyclic aliphatic acetal group, cyclic lactone group, cyclic thioether group, spiro-ortho ester group, and vinyloxy group. Among these, an alicyclic ether group and vinyloxy group are preferable; and an epoxy group, oxetanyl group and vinyloxy group are more preferable. In the formula, $P^1$ and $P^2$ may be different from each other, or, that is, the compound represented by formula (I) may have two or more types of polymerizable groups. In such a case, the compound may have polymerizable groups of which polymerization mechanisms are different from each other, for example, a radical polymerizable group and a cationic polymerizable group, or may have polymerizable groups of which polymerization mechanisms are same.

Preferably, $P^1$ and $P^2$ each independently represent any one of groups of (P-1)-(P-5).

(P-1)

-continued

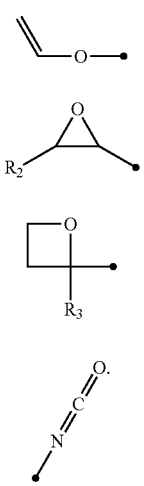

(P-2)

(P-3)

(P-4)

(P-5)

In the formulas, $R^1$-$R^3$ each independently represent a hydrogen atom or methyl.

Preferably, $P^1$ and $P^2$ each independently represent a (meth)acrylate group, or, that is, represent any of the groups shown below.

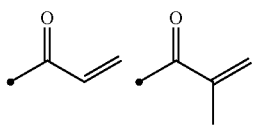

In the formula, m1 and m2 each independently represent an integer of from 1 to 10, preferably from 2 to 8, or more preferably from 3 to 6.

And one $CH_2$ or two or more $CH_2$, which may be not adjacent to each other, in —$(CH_2)_{m1}$— and —$(CH_2)_{m2}$— may be replaced with —O— or —S—.

In the formula, "A" represents a divalent group having a 5- to 18-membered aromatic hydrocarbon ring or a 5- to 18-membered aromatic hetero ring. The aromatic hydrocarbon ring or the aromatic hetero ring may be a monocyclic structure or condensed ring structure. The monocyclic structure is preferably a 5- to 7-membered cyclic structure, or more preferably, a 5- or 6-membered cyclic structure. The hetero atom embedded in the hetero ring is preferably one or two selected from nitrogen, oxygen and sulfur atoms. "A" may have two or more cyclic structures which may be same or different from each other, and in such a case, the cyclic structures may be linked by a single bond or a divalent group. Examples of the divalent group include ethenyl, carbonyl, acetylene, schiff, and azo group.

Examples of "A" include, but are not limited, those shown below.

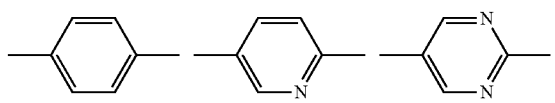

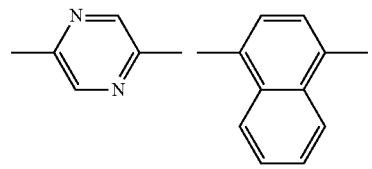

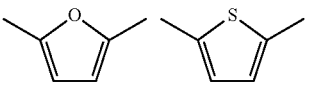

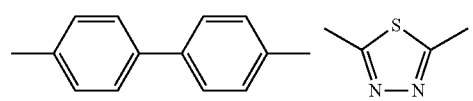

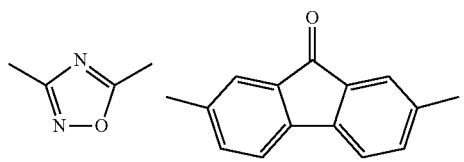

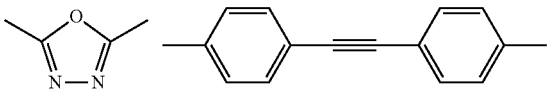

In the formula, preferably, "A" represents a divalent group having a 6-membered aromatic hydrocarbon ring, more preferably, "A" represents phenylene, or even more preferably, "A" represents 1,4-phenylene.

At least one hydrogen atom contained in "A" may be replaced with a $C_{1-4}$ alkyl group such as methyl, ethyl, n- and iso-propyl, and n-, iso- and tert-butyl; $C_{1-4}$ alkoxy group such as methoxy, ethoxy, n- and iso-propoxy, and n-, iso- and tert-butoxy; or halogen atom such as fluorine, chlorine, bromine and iodine atom.

In the formula, $L^3$ and $L^4$ each independently represent a $C_{1-10}$ alkyl group or a $C_{1-10}$ alkoxy group. The number of carbon atoms in the alkyl or alkoxy group is preferably from 1 to 4, and preferable examples thereof include methyl, ethyl, n- and iso-propyl, n-, iso- and tert-butyl, methoxy, ethoxy, n- and iso-propoxy, and n-, iso- and tert-butoxy.

In the formula, k1 and k2 each independently represent an integer of from 0 to 4, preferably from 0 to 2, or more preferably 0 or 1. When K1 and k2 are 1, the compound preferably has the alkyl, alkoxy or halogen atom at the meta-position with respect to the position of the cinnamate group.

In the formula, n1 and n2 each independently represent 0 or 1, provided that at least one of them is 1. Or that is, the compound represented by formula (I) is a compound having at least one cinnamate group.

Examples of the compound represented by formula (I) include the compounds represented by formulas (Ia) and (Ib). in terms of achieving high Δn, the compound represented by formula (Ia) is more preferable.

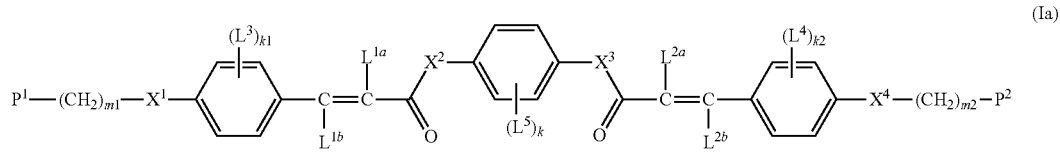

(Ia)

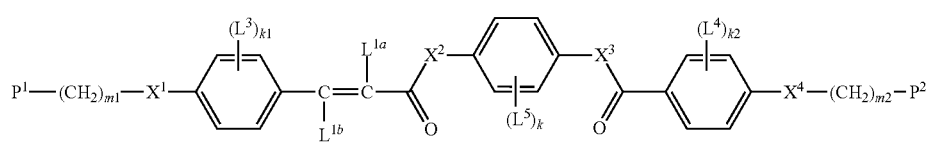

(Ib)

In the formula, $L^5$ each represents a $C_{1-4}$ alkyl group such as methyl, ethyl, n- and iso-propyl, and n-, iso- and tert-butyl, $C_{1-4}$ alkoxy group such as methoxy, ethoxy, n- and iso-propoxy, and n-, iso- and tert-butoxy; or halogen atom such as fluorine, chlorine, bromine and iodine atom. In the formula, k each represents an integer of from 0 to 4.

In the formulas (I), (Ia) and (Ib), $L^{1a}$, $L^{1b}$, $L^{2a}$ and $L^{2b}$ each independently represent a hydrogen atom, halogen atom, —CN, —NC, —NCO, —NCS, or —OCN, or preferably represent a hydrogen atom or —CN.

In the formulas, $X^1$, $X^2$, $X^3$ and $X^4$ each independently represent —O—, —S—, —NH—, —NR— or —SiR$^0$R$^{00}$—; and R, $R^0$ and $R^{00}$ each independently represent a $C_{1-10}$ (preferably $C_{1-4}$) alkyl group such as methyl, ethyl, n- and iso-propyl, and n-, iso- and tert-butyl.

However, those in which both of $X^2$ and $X^3$ represent —O—, those in which one of $X^2$ and $X^3$ represents —O— and another represents —NH— or —NR— are excluded only when n1 is 1, both of $L^{1a}$ and $L^{1b}$ are hydrogen atoms, n2 is 1, and both of $L^{2a}$ and $L^{2b}$ are hydrogen atoms (or that is, when, in formula (Ia), both of $L^{1a}$ and $L^{1b}$ are hydrogen atoms, and both of $L^{2a}$ and $L^{2b}$ are hydrogen atoms), or only when n1 is 1, both of $L^{1a}$ and $L^{1b}$ are hydrogen atoms, and n2 is 0 (or that is, when, in formula (Ib), both of $L^{1a}$ and $L^{1b}$ are hydrogen atoms).

Preferably, at least one of $X^2$ and $X^3$ represents —S—, or more preferably, one of $X^2$ and $X^3$ represents —S—, and another of $X^2$ and $X^3$ represents —O—.

The compounds in which at least one of $X^2$ and $X^3$ represent —S— are preferable, and the compounds in which one of $X^2$ and $X^3$ represents —S— and another represents —O— are more preferable, when n1 is 1, both of $L^{1a}$ and $L^{1b}$ are hydrogen atoms, n2 is 1, and both of $L^{2a}$ and $L^{2b}$ are hydrogen atoms (or that is, when, in formula (Ia), both of $L^{1a}$ and $L^{1b}$ are hydrogen atoms, and both of $L^{2a}$ and $L^{2b}$ are hydrogen atoms), or when n1 is 1, both of $L^{1a}$ and $L^{1b}$ are hydrogen atoms, and n2 is 0 (or that is, when, in formula (Ib), both of $L^{1a}$ and $L^{1b}$ are hydrogen atoms).

Preferable examples of the compound represented by formula (I) include the compounds represented by formulas (Ia-1) and (Ia-2) and by formulas (Ib-1) and (Ib-2). Among the compounds represented by formula (Ia), in terms of achieving higher Δn, the compounds represented by formula (Ia-1) are more preferable. Among the compounds represented by formula (Ib), in terms of achieving higher Δn, the compounds represented by formula (Ib-1) are more preferable.

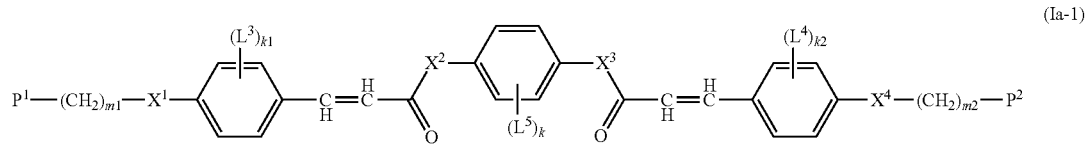

(Ia-1)

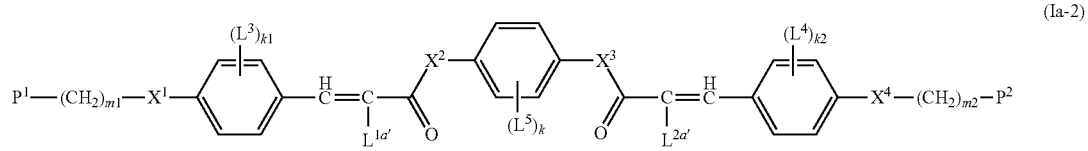

(Ia-2)

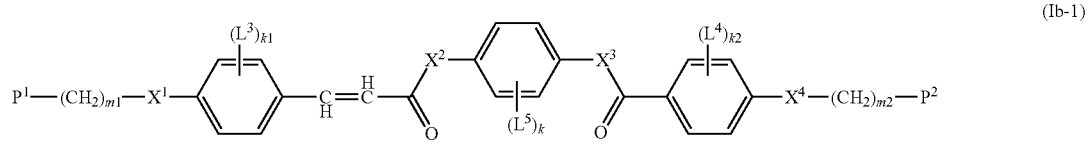

(Ib-1)

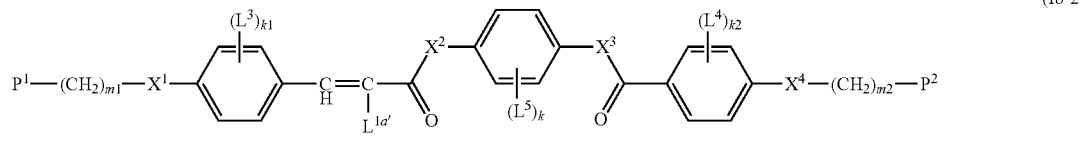

(Ib-2)

The definitions of the symbols in the formulas are same as those in the formulas (I), (Ia), and (Ib), and their preferable ranges are same as those in the (I), (Ia) and (Ib). In the formulas, $X^{2'}$ represents —S—, —NH—, —NR— or —SiR$^0$R$^{00}$—. Preferably, $X^{2'}$ is —S—, and $X^3$ is —O—. In the formulas, $L^{1a'}$ represents a halogen atom, —CN, —NC, —NCO, —NCS or —OCN. Preferably, $L^{1a'}$ is —CN.

Preferable examples of the compound represented by formula (I) include the compounds represented by formulas (Ia-3), (Ia-4), (Ia-5) and (Ia-6), and by formulas (Ib-3), (Ib-4) and (Ib-5). Among the compounds represented by formula (Ia), in terms of achieving higher Δn, the compounds represented by formula (Ia-3) are more preferable. Among the compounds represented by formula (Ib), in terms of achieving higher Δn, the compounds represented by formula (Ib-3) are more preferable.

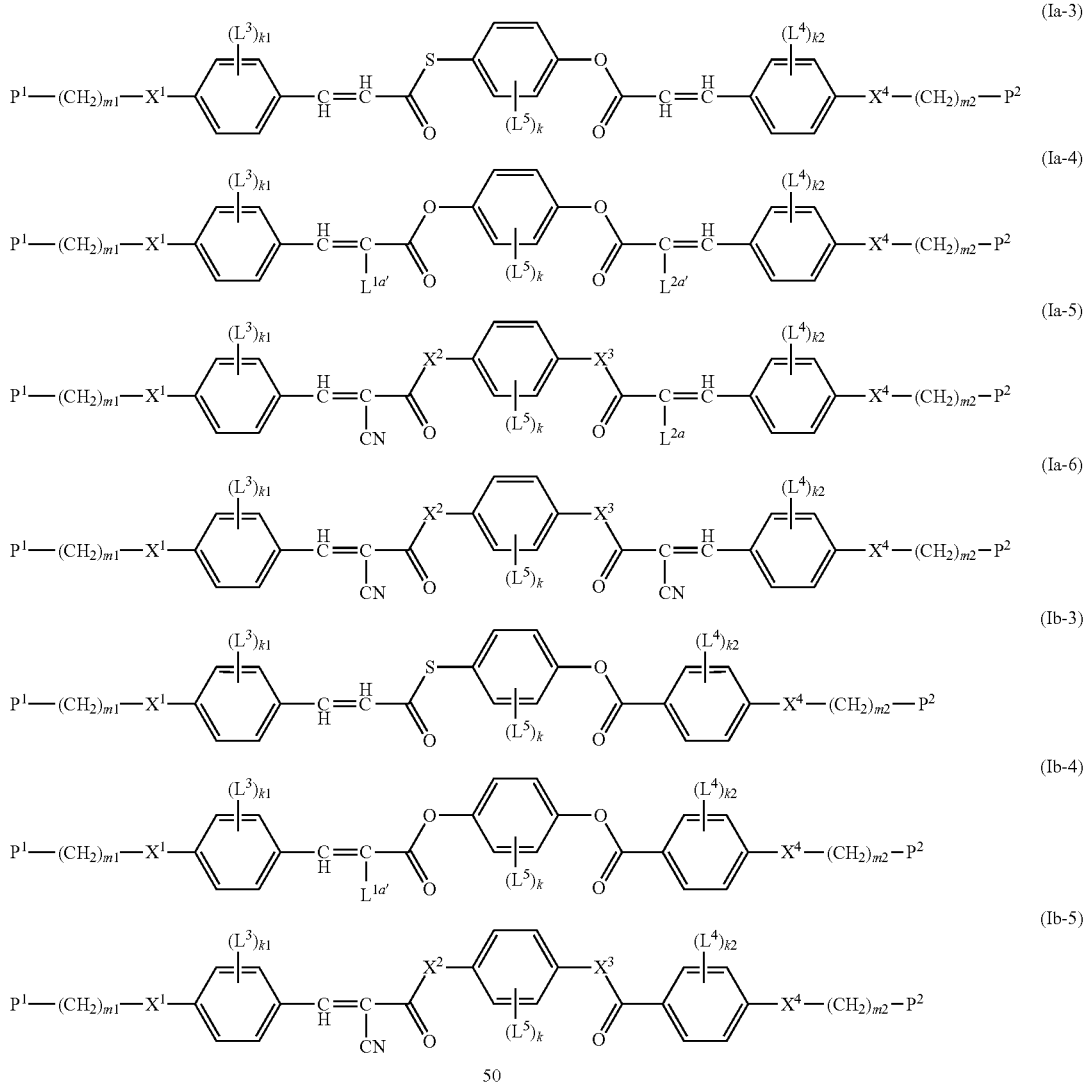

The definitions of the symbols in the formulas are same as those in the formulas (I), (Ia), (Ib), Ia-1), (Ia-2), (Ib-1) and (Ib-2); and their preferable ranges are same as those in the (I), (Ia), (Ib), Ia-1), (Ia-2), (Ib-1) and (Ib-2). In the formulas, preferably, $X^2$ and $X^3$ represents —O—. Preferably, $L^{1a'}$ is —CN.

Examples of the compound represented by formula (I) include, but are not limited, those shown below.

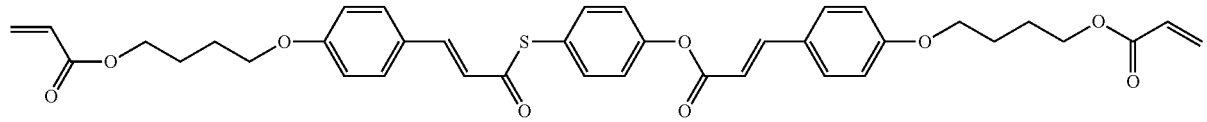

(I-2)
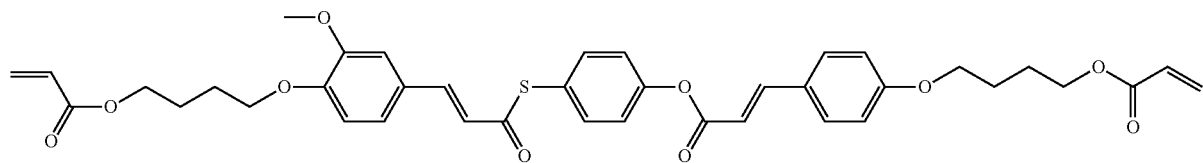
(I-3)
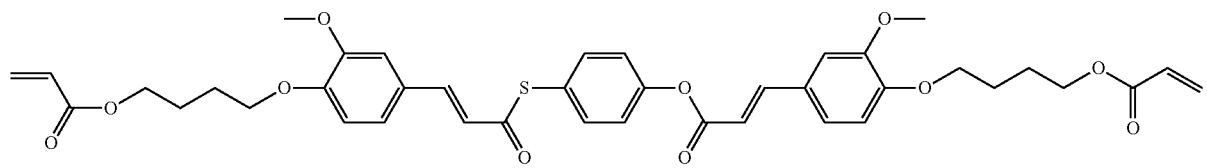
(I-4)
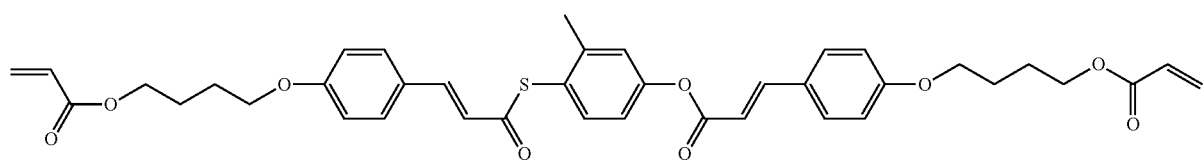
(I-5)
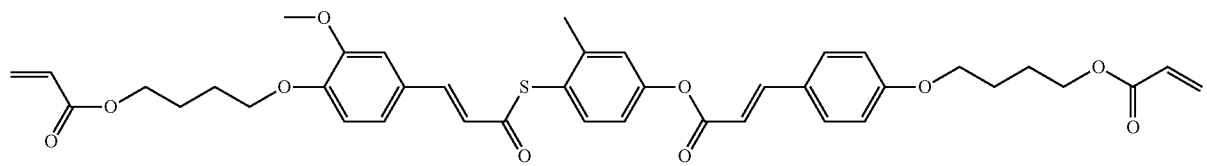
(I-6)
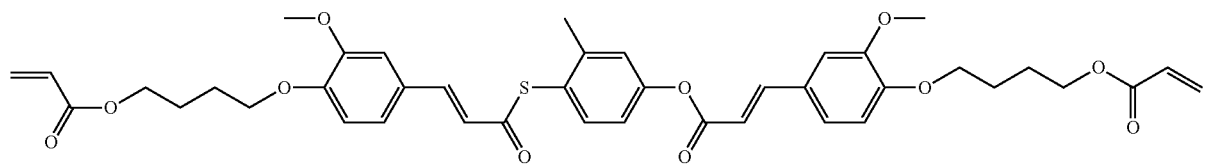
(I-7)
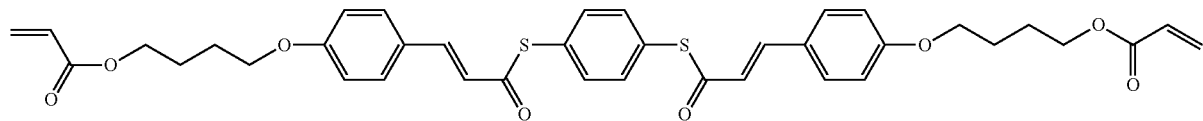
(I-8)
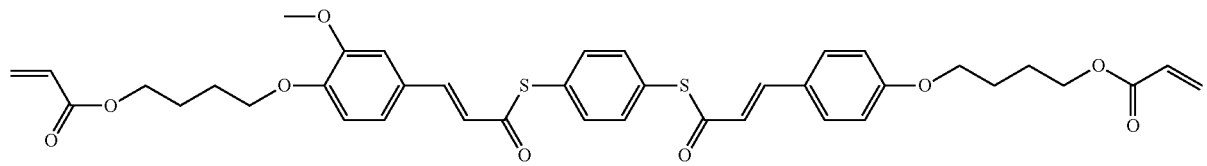
(I-9)
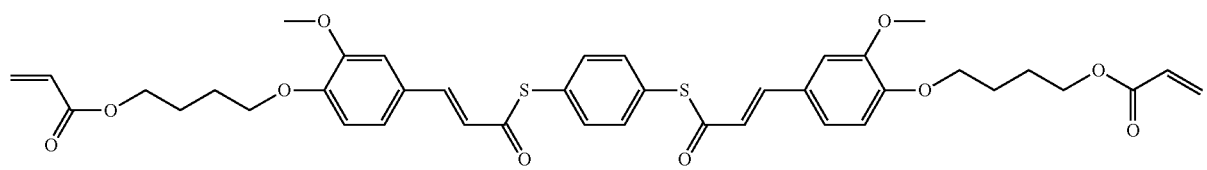

(I-10)
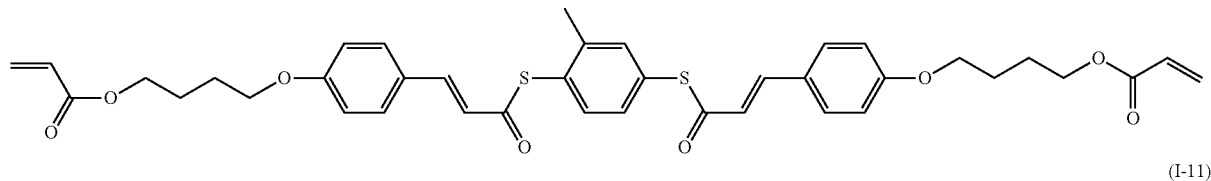
(I-11)
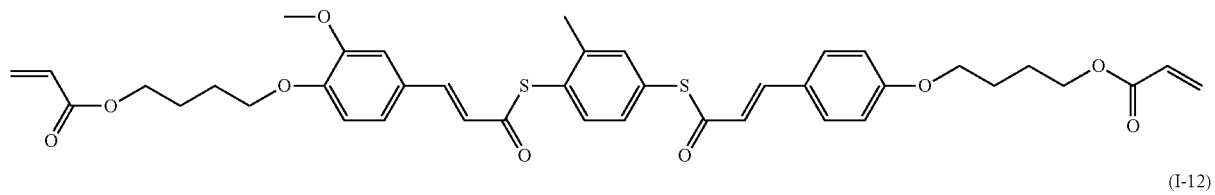
(I-12)
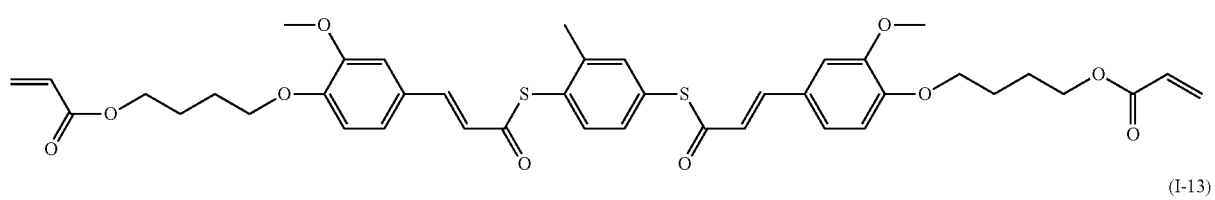
(I-13)
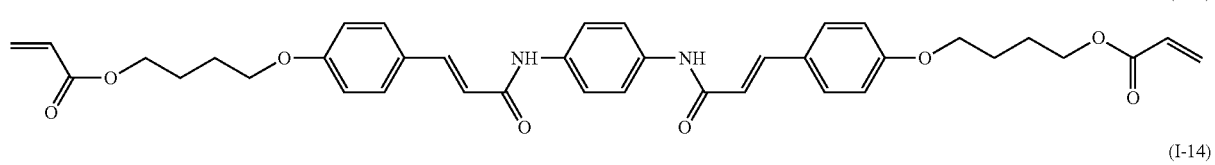
(I-14)
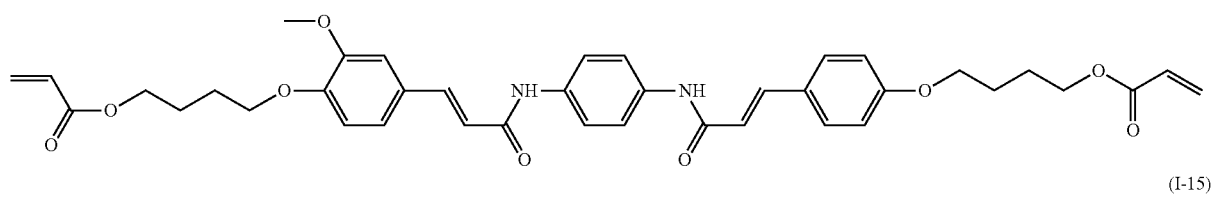
(I-15)
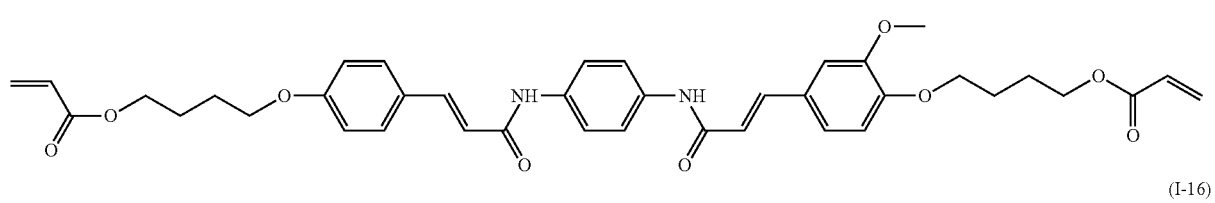
(I-16)
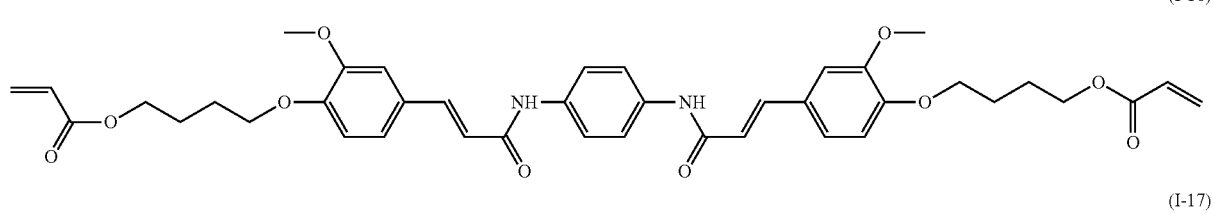
(I-17)
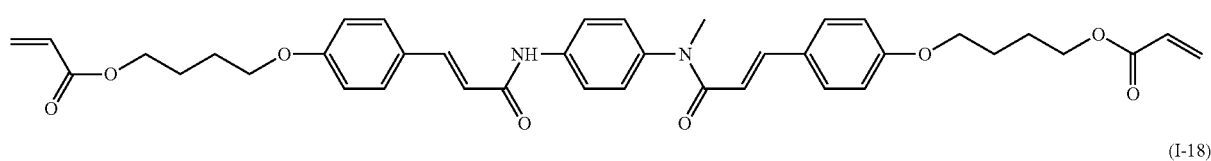
(I-18)
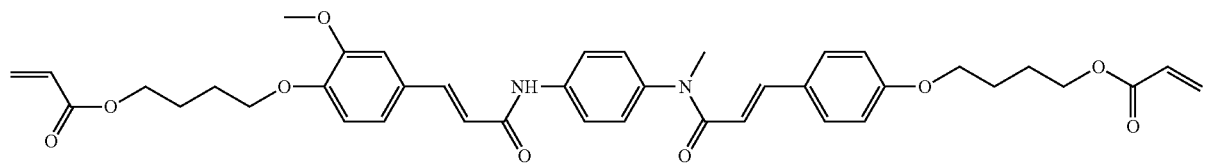

(I-19)
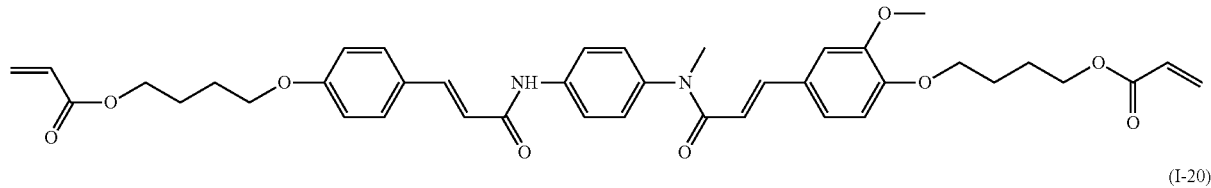
(I-20)
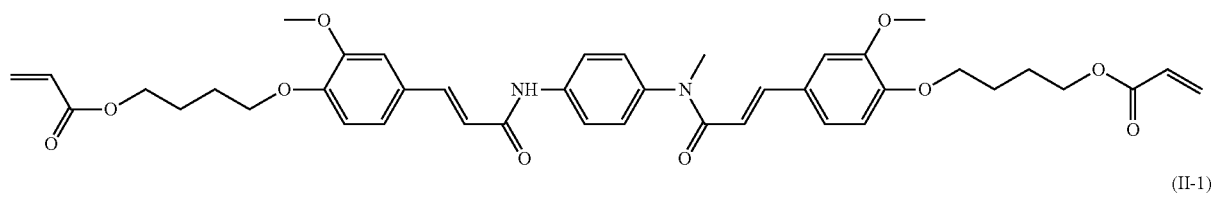
(II-1)
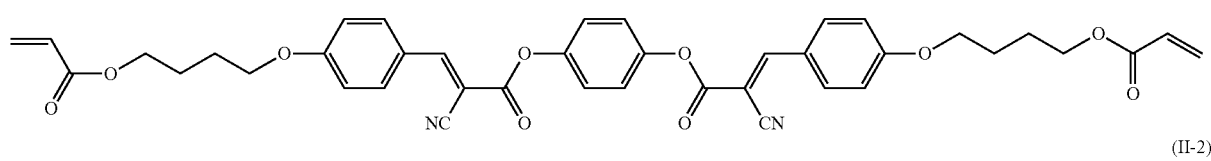
(II-2)
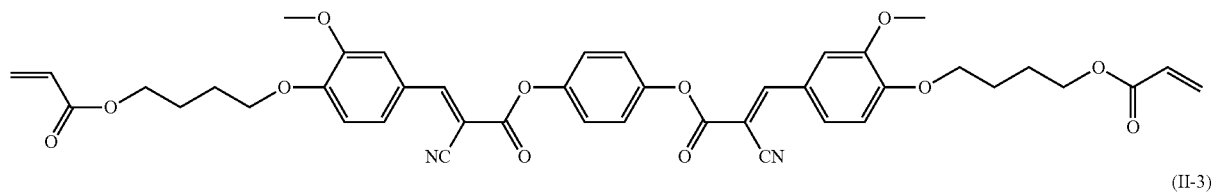
(II-3)
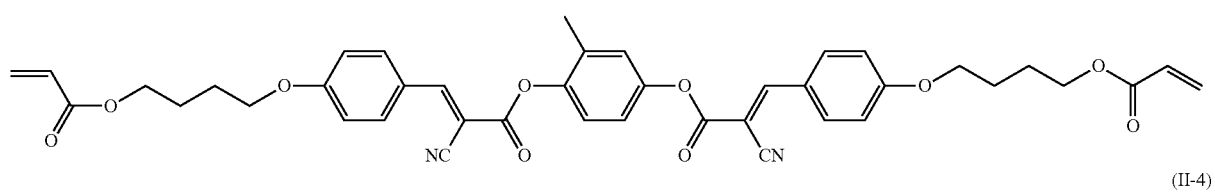
(II-4)
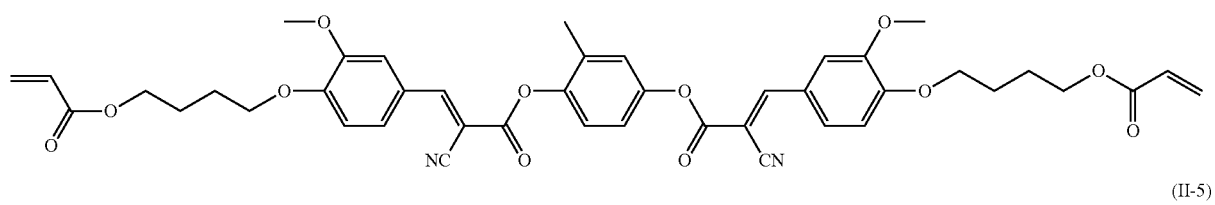
(II-5)
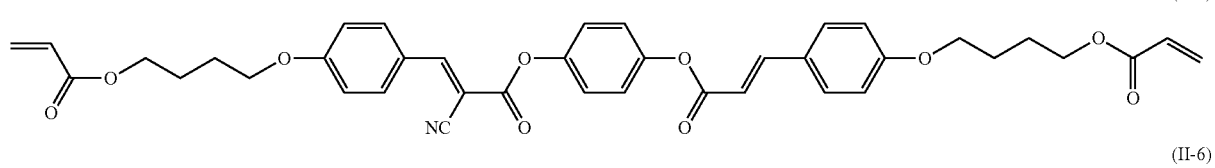
(II-6)
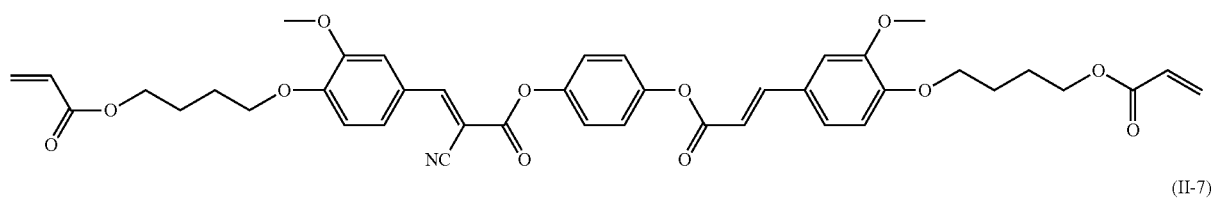
(II-7)
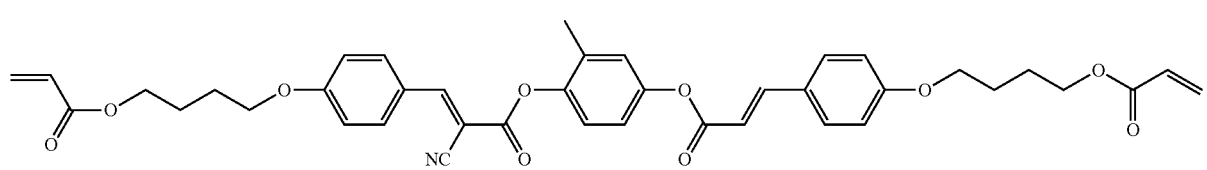

-continued
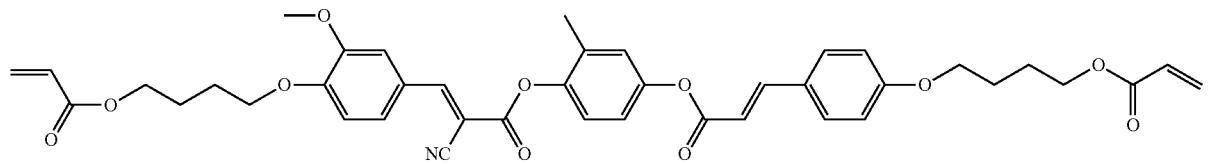
(II-8)
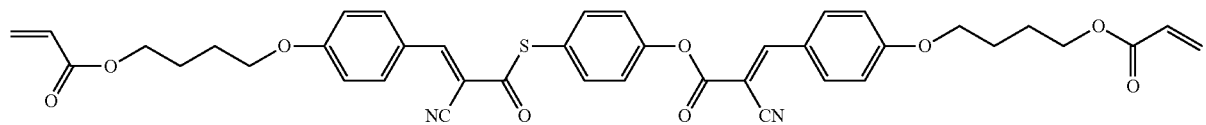
(II-9)
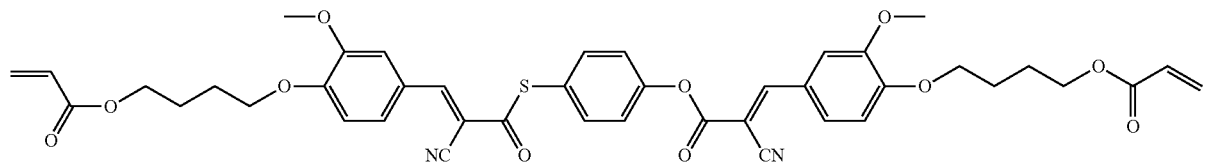
(II-10)
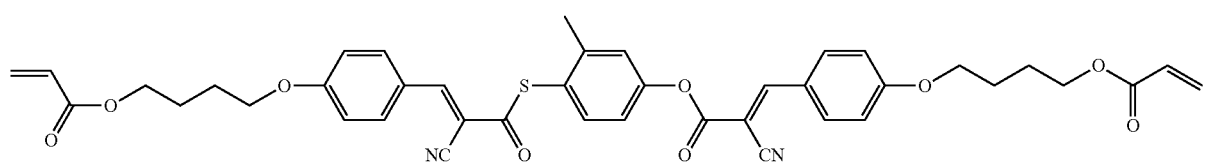
(II-11)
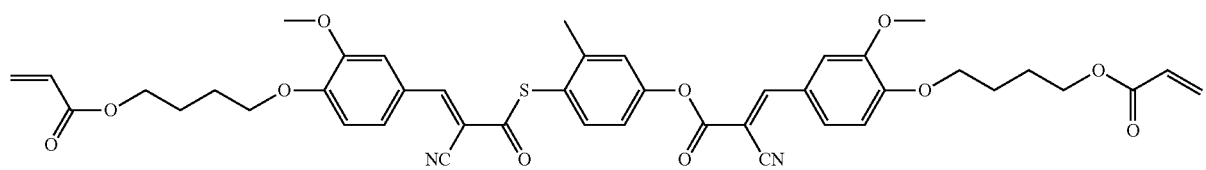
(II-12)
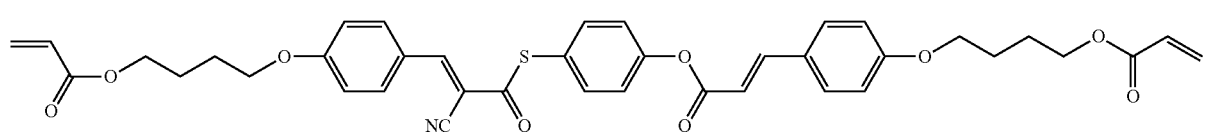
(II-13)
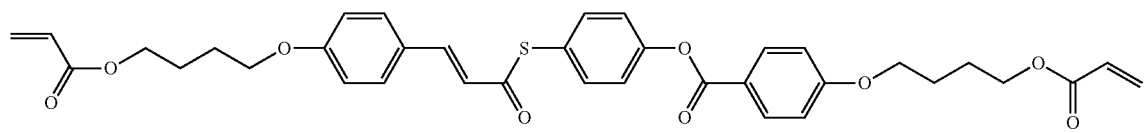
(III-1)
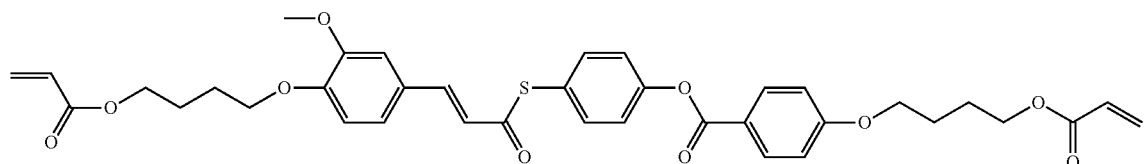
(III-2)
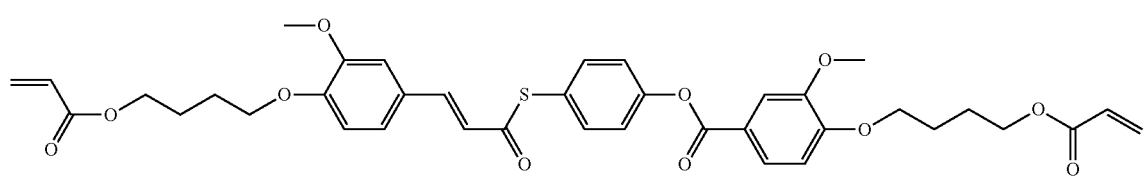
(III-3)

-continued
(III-4)
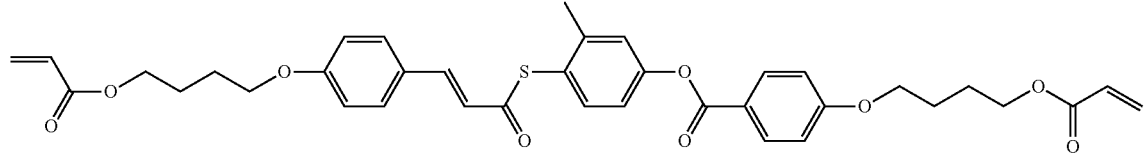
(III-5)
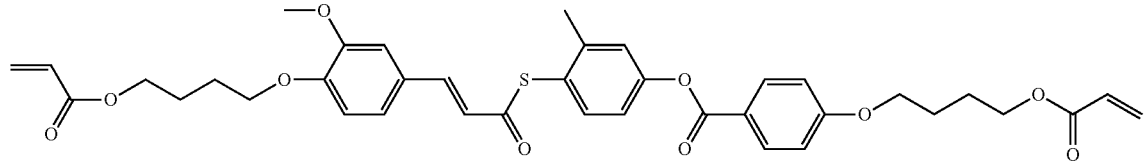
(III-6)
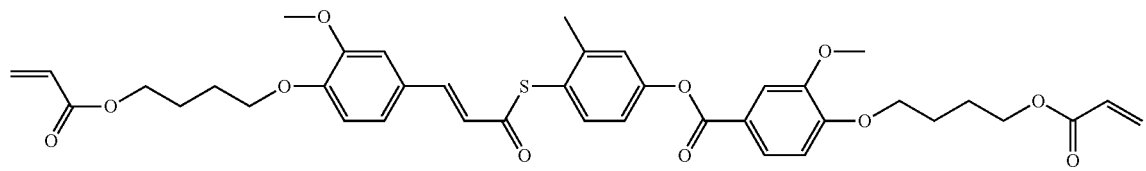
(III-7)
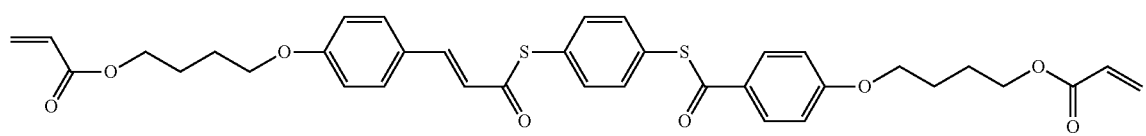
(III-8)
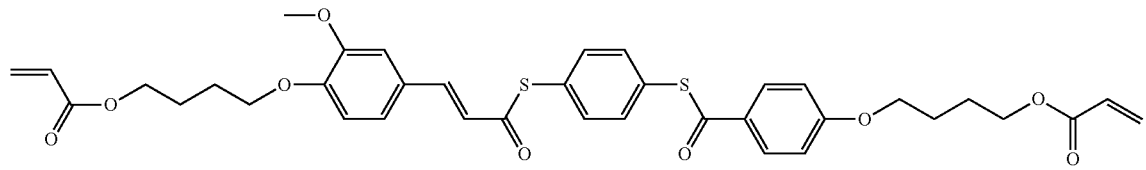
(III-9)
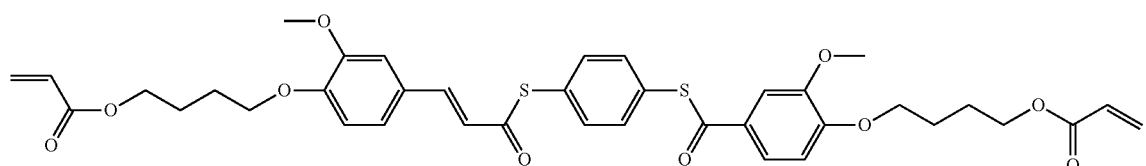
(III-10)
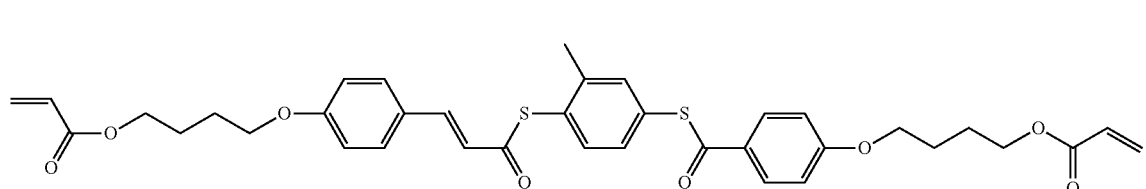
(III-11)
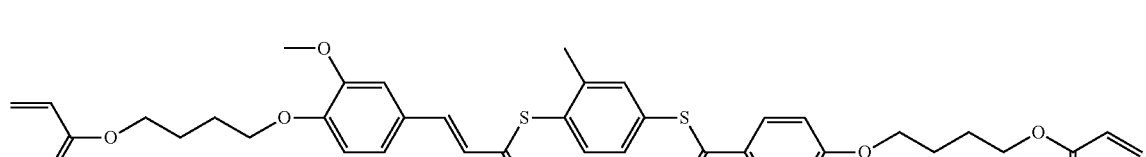
(III-12)
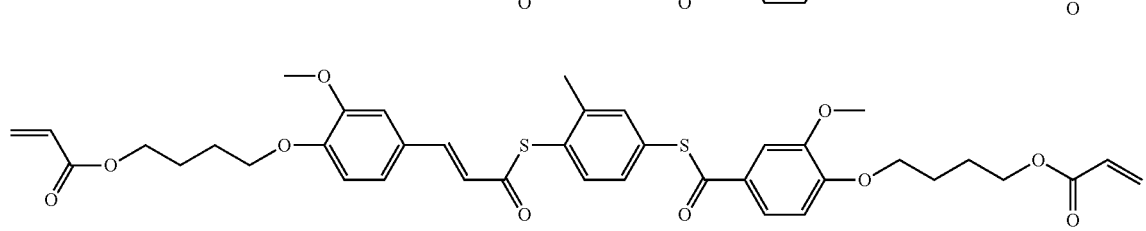

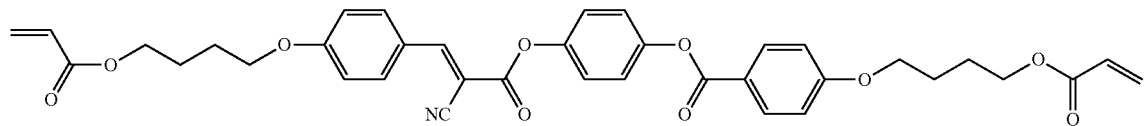
(IV-1)
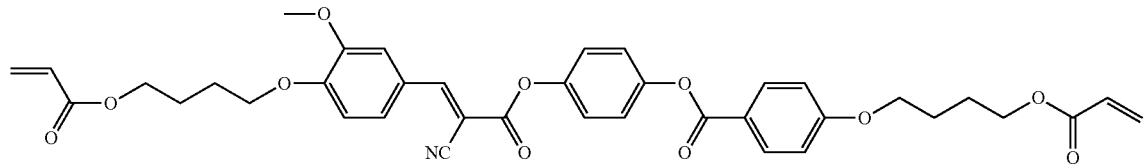
(IV-2)
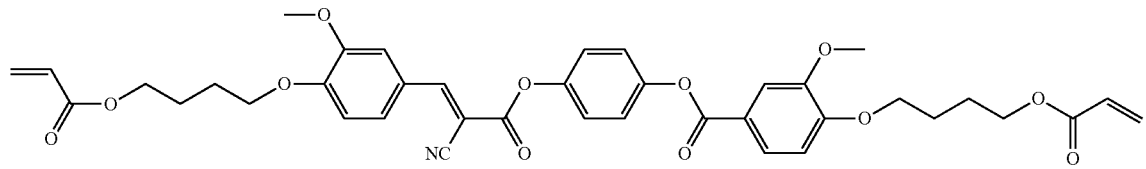
(IV-3)
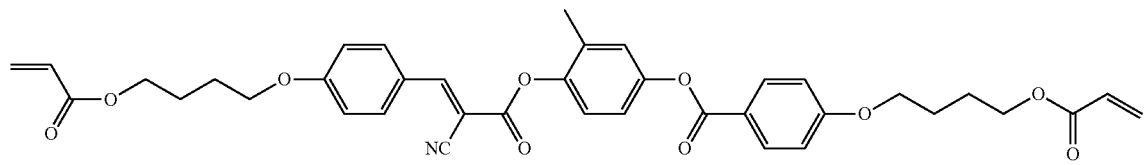
(IV-4)
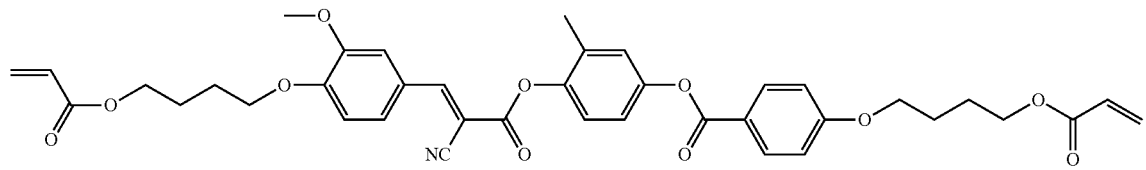
(IV-5)
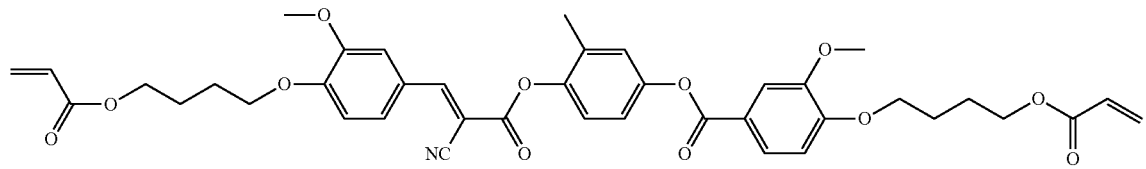
(IV-6)
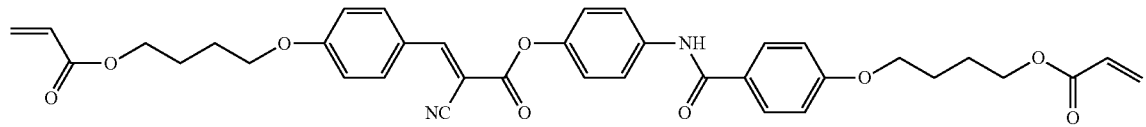
(IV-7)
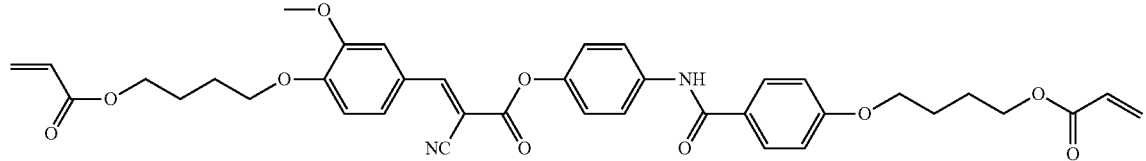
(IV-8)
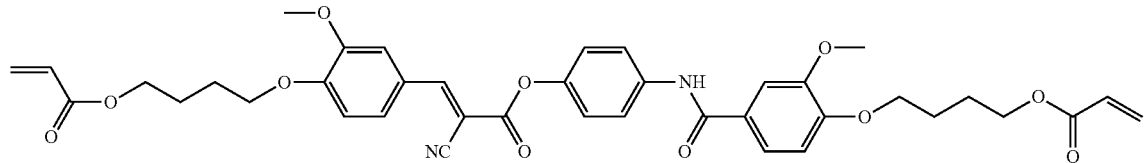
(IV-9)

(IV-10)
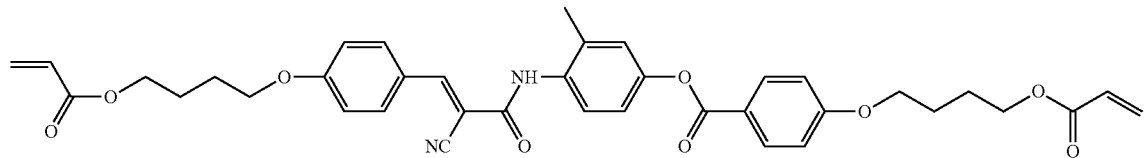
(IV-11)
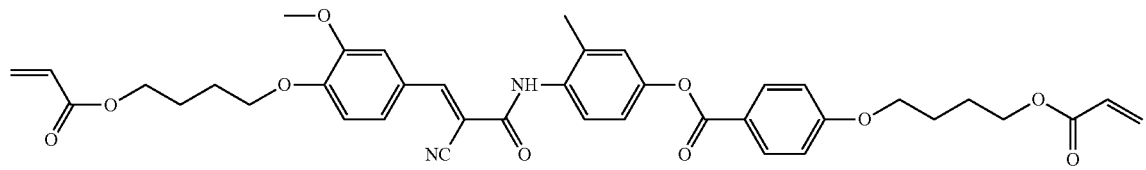
(IV-12)
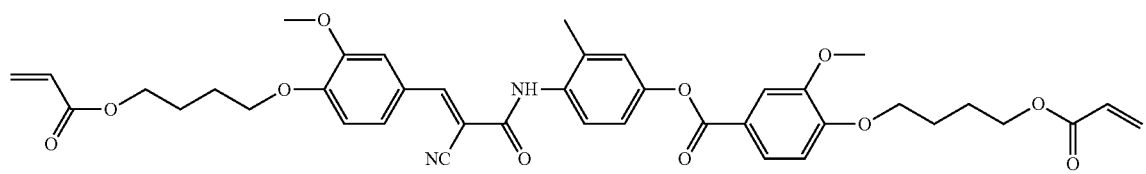
(V-1)
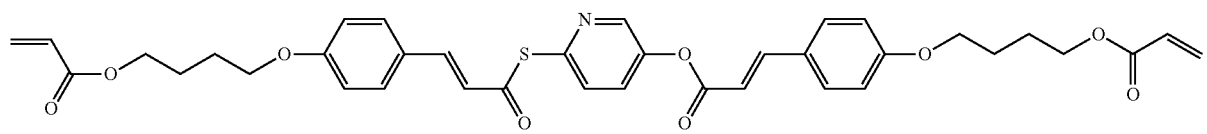
(V-2)
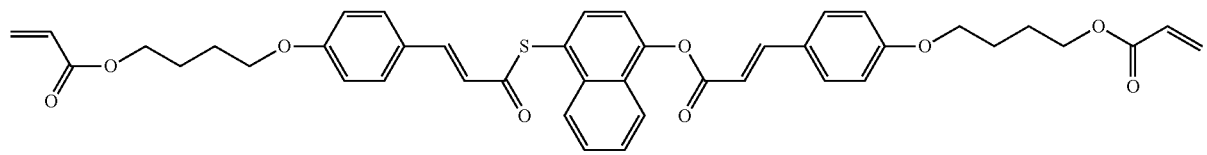
(V-3)
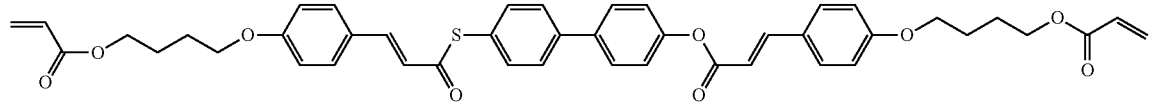
(V-4)
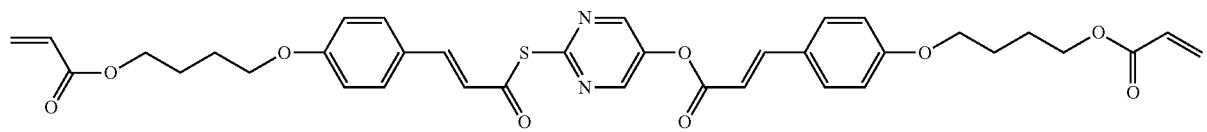
(V-5)
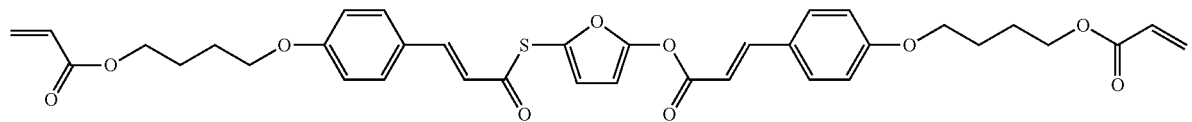
(V-6)
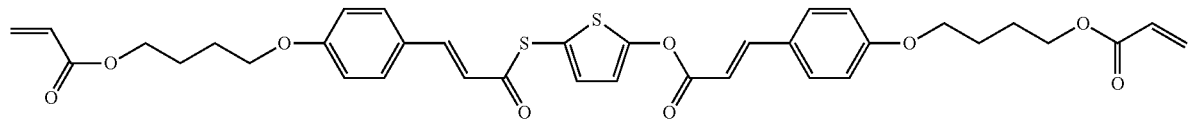

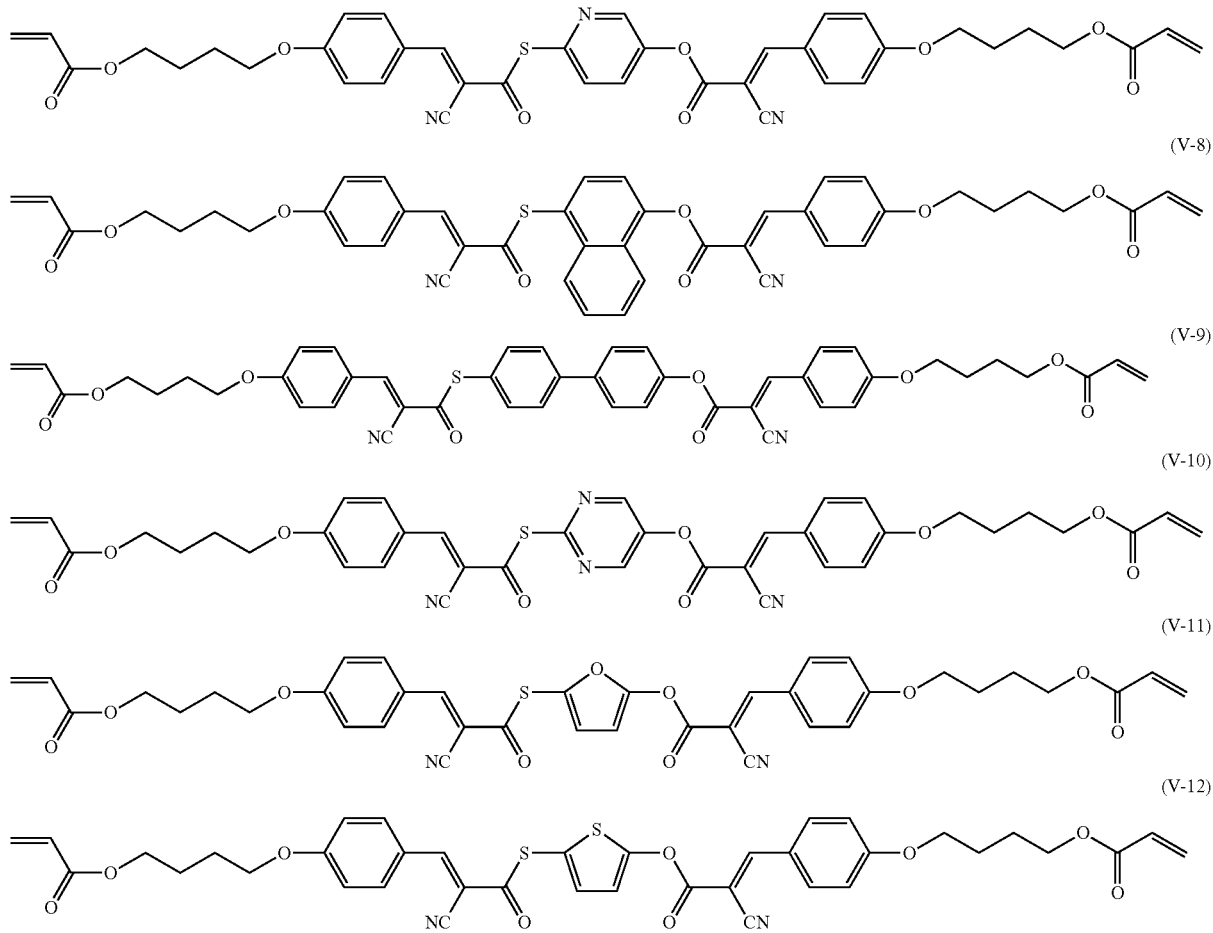

The compound represented by formula (I) may be prepared by combining any organic synthetic reactions.

One example of the method for preparing the compound represented by formula (I), having two or more cinnamate groups, is as follows. An intermediate represented by formula (II) shown below is prepared, and then, one or more types of the intermediates are reacted with arbitrary reagent.

The compound represented by formula (I), having one cinnamate group, may be prepared by reacting an intermediate represented by formula (III) shown below along with an intermediate represented by formula (II) with arbitrary reagent.

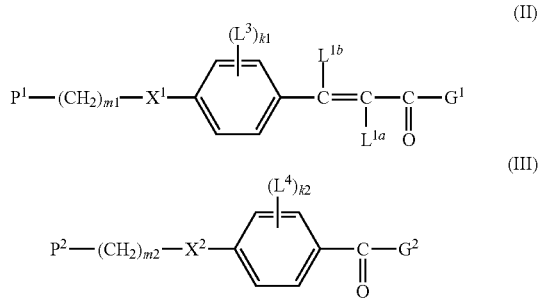

The definitions of the symbols in formula (II) are same as those in formula (I) respectively, and $G^1$ and $G^2$ each independently represent a reactive group such as amino, hydroxy and mercapto, which can react with arbitrary reagent to form the group of —$X^2$— or —$X^3$— in formula (I).

The intermediate represented by formula (II) may be prepared by referring the method described in Japanese Patent No. 4355406, p. 23, [0109]-[0110].

The intermediate represented by formula (III) may be prepared by referring the method described in JP-A-2002-97170, p. 10, [0085]-[0087].

The polymerizable liquid crystal compound of the invention shows high Δn, and the film of the cured alignment of the compound may achieve the desired optical properties with a thinner thickness, compared with the film of the cured alignment of a liquid crystal compound having low Δn.

The polymerizable compound of the invention is chemically stable, is easily dissolved in solvent, is easily polymerized, and is colorless and transparent; and therefore, the compound of the invention is excellent in plural properties. The cured film prepared by using the compound of the invention may have a sufficient hardness, be colorless and transparent, and be excellent in weather resistance and in heat resistance; and therefore, the film may be excellent in plural properties. Accordingly, the cured film prepared by using the compound of the invention may be used in various technical fields of optical elements such as retardation plates, polarizing elements, selective reflection films, color filters, anti-reflection films, optical compensation films, holography, and alignment layers.

2. Polymerizable Liquid Crystal Composition and Film

The present invention relates to a polymerizable liquid crystal composition containing at least one compound represented by formula (I), and to a film formed of the composition. The composition of the invention is useful as a material for optical films such as retardation films and reflective films.

One embodiment of the polymerizable liquid crystal composition of the invention contains at least one compound represented by formula (I) and at least one chiral compound. The film, which is formed by curing the cholesteric liquid crystal alignment of the embodiment, may exhibit selective reflection ascribed to the helical pitch, which is useful as a reflective film (for example, IR reflective film). By using the polymerizable liquid crystal compound showing high Δn, the film having a thickness may exhibit reflection for the broader wavelength region, compared with a film having the same thickness prepared by using a liquid crystal compound showing low Δn.

In the composition of the invention, the compound represented by formula (I) may be a major ingredient or additive. An amount of the compound represented by formula (I) is preferably equal to or more than 5 mass % with respect to the total mass of the composition in terms of obtaining the effect of the compound, more preferably is from 10 to 85 mass %, even more preferably is from 10 to 75 mass %, or even much more preferably is from 15 to 70 mass %. However, an amount of the compound of the invention in the composition is not limited.

(1) Chiral Compound

For preparing the liquid crystal composition of the invention capable of forming a cholesteric liquid crystal phase, preferably, at least one chiral compound may be added to the composition. The chiral compound may be selected from liquid crystal compounds or non-liquid crystal compounds. The chiral compound may be selected from any known chiral agents such as those used in twisted-nematic (TN) and super-twisted-nematic (STN) modes, which are described, for example, in "Ekisho Debaisu Handobukku (Liquid Crystal Device Handbook)", Third Chapter, 4-3 Chapter, p. 199, edited by No. 142 Committee of Japan Society for the Promotion of Science, published by the Nikkan Kogyo Shimbun, Ltd., in 1989. Although, generally, a chiral compound has a chiral carbon in its molecule, axially chiral compounds and planar chiral compound, having no chiral carbon, may be used as a chiral compound in the invention. Examples of the axially chiral compound or the planar chiral compound include binaphthyl, helicene, para cyclophane and derivatives thereof. The chiral compound (chiral agent) may have at least one polymerizable group. Using a polymerizable chiral compound along with a polymerizable rod-like compound, it is possible to obtain a polymer having repeating units derived from the optically-active compound and the rod-like liquid crystal compound respectively by carrying out the polymerization thereof. In such an embodiment, the polymerizable group in the chiral compound is preferably same as that in the rod-like liquid crystal compound. Accordingly, the polymerizable group in the optically-active compound is preferably selected from an unsaturated polymerizable group, epoxy group and aziridinyl group; and an unsaturated polymerizable group is preferable; and an ethylene unsaturated polymerizable group is especially preferable.

An amount of the chiral compound is preferably from 1 to 30% by mole with respect to an amount of the liquid crystal compound represented by formula (I) used along with it. A smaller amount of the chiral compound is more preferable since influence thereof on liquid crystallinity may be small. Accordingly, chiral compounds having a strong helical twisting power are preferable since they may achieve the desired helical pitch by being added in a small amount. Examples of such a chiral compound having a strong helical twisting power include those described in JPA 2003-287623.

(2) Other Liquid Crystal Compounds

The composition of the invention may contain at least one liquid crystal compound other than formula (I) along with the compound of formula (I). The compound represented by formula (I) exhibits high compatibility with another liquid crystal compound, may not become opacified even if being mixed with other liquid crystal compound(s), and may form a transparent film. According to the invention, the composition may contain other liquid crystal compound(s) along with the compound represented by formula (I), and may be used in various applications. Examples of other liquid crystal compound which can be used along with the compound represented by formula (I) include azomethines, azoxys, cyanobiphenyls, cyanophenyl esters, benzoic acid esters, cyclohexanecarboxylic acid phenyl esters, cyanophenylcyclohexanes, cyano-substituted phenylpyrimidines, alkoxy-substituted phenylpyrimidines, phenyl dioxanes, tolans and alkenylcyclohexyl benzonitriles. In the invention, the liquid crystal compound can be selected from not only low-molecular weight compounds but also high-molecular weight compounds.

Other liquid crystal compound which can be used along with the compound represented by formula (I) may be polymerizable or not polymerizable. Examples of the rod-like liquid crystal having no polymerizable group are described in many documents such as Y. Goto et. al., Mol. Cryst. Liq. Cryst. 1995, Vol. 260, pp. 23-28.

A polymerizable rod-like liquid crystal compound may be prepared by introducing a polymerizable group in rod-liquid crystal compound. Examples of the polymerizable group include an unsaturated polymerizable group, epoxy group, and aziridinyl group; and an unsaturated polymerizable group is preferable; and an ethylene unsaturated polymerizable group is especially preferable. The polymerizable group may be introduced in a rod-like liquid crystal compound according to any method. The number of the polymerizable group in the polymerizable rod-like liquid crystal compound is preferably from 1 to 6 and more preferably from 1 to 3. Examples of the polymerizable rod-like liquid crystal compound include those described in Makromol. Chem., vol. 190, p. 2255 (1989), Advanced Materials, vol. 5, p. 107 (1993), U.S. Pat. Nos. 4,683,327, 5,622,648, 5,770,107, WO95/22586, WO95/24455, WO97/00600, WO98/23580, WO98/52905, JPA No. 1-272551, JPA No. 6-16616, JPA No. 7-110469, JPA No. 11-80081 and JPA No. 2001-328973. Plural types of polymerizable rod-like liquid crystal compounds may be used in combination. Using plural types of polymerizable rod-like liquid crystal compounds may contribute to lowering the alignment temperature.

An amount of other liquid crystal compound(s) is not limited. Any embodiments, in which an amount of the liquid crystal compound represented by formula (I) is higher or smaller than or same as that of other liquid crystal compound(s), may be prepared depending on their applications.

(3) Polymerization Initiator

The composition of the invention preferably contains at least one polymerization initiator. According to the invention, the polymerization may be carried out under irradiation of ultraviolet light, and the polymerization initiator is preferably selected from photo-polymerization initiators capable of initiating polymerizations by irradiation of ultraviolet light. Examples of the photo-polymerization initiator include α-carbonyl compounds (those described in U.S. Pat. Nos. 2,367,661 and 2,367,670), acyloin ethers (those described in U.S. Pat. No. 2,448,828), α-hydrocarbon-substituted aromatic acyloin compounds (those described in U.S. Pat. No. 2,722,512), polynuclear quinone compounds (those described in U.S. Pat. Nos. 3,046,127 and 2,951,758), combinations of triarylimidazole dimer and p-aminophenyl ketone (those described in U.S. Pat. No. 3,549,367), acrydine and phenazine compounds (those described in Japanese Laid-Open Patent Publication "Tokkai" No. S60-105667 and U.S. Pat. No. 4,239,850), and oxadiazole compounds (those described in U.S. Pat. No. 4,212,970).

An amount of the photo-polymerization initiator is preferably from 0.1 to 20% by mass, more preferably from 1 to 8% by mass, with respect to the liquid crystal composition (the solid content when the composition is a coating liquid).

(4) Alignment Controlling Agent

Any alignment controlling agent, which can contribute to stably or promptly forming a liquid crystal phase such as a cholesteric liquid crystal phase, may be added to the liquid crystal composition of the invention. Examples of the alignment controlling agent include fluorine-containing (meth) acrylate series polymers and compounds represented by formula (X1)-(X3). Two or more types selected from these compounds may be used in combination. These compounds may contribute to aligning liquid crystal molecules with a small tilt angle or horizontally at the air-interface alignment. It is to be understood that the term "horizontal alignment" in the specification means that the direction of long axis of a liquid crystalline molecule is parallel to the layer plane, wherein strict parallelness is not always necessary; and means, in this specification, that a tilt angle of the mean direction of long axes of liquid crystalline molecules with respect to the horizontal plane is smaller than 20°. The layer in which liquid crystal molecules are horizontally aligned at the air-interface may hardly suffer from alignment defects, and may have a high transparency for a visible light and have a high reflection rate. On the other hand, the layer in which liquid crystal molecules are aligned with a large tilt angle may suffer from the finger-print pattern, and may have a low reflective rate, high haze and diffraction characteristics, because of the misalignment between the helical axis of the cholesteric liquid crystal phase and the normal line of the layer surface.

Examples of the fluorine-containing (meth)acrylate series polymer, which can be used as an alignment controlling agent, include those described in JPA 2007-272185, [0018]-[0043].

The compounds represented by formula (X1)-(X3), which can be used as an alignment controlling agent, will be described in detail respectively.

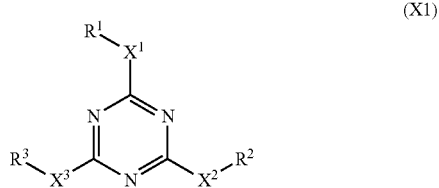

(X1)

In the formula, $R^1$, $R^2$ and $R^3$ each independently represent a hydrogen atom or a substituent group; $X^1$, $X^2$ and $X^3$ each independently represent a single bond or divalent linking group. The substituent group represented by $R^1$-$R^3$ respectively is preferably a substituted or non-substituted alkyl group (more preferably a non-substituted alkyl or a fluorinated alkyl group), an aryl group (more preferably an aryl group having at least one fluorinated alkyl group), a substituted or non-substituted amino group, an alkoxy group, an alkylthio group, or a halogen atom. The divalent linking group represented by $X^1$, $X^2$ and $X^3$ respectively is preferably selected from the group consisting of an alkylene group, an alkenylene group, a divalent aryl group, a divalent heterocyclic group, —CO—, —NR$^a$— (where $R^a$ represents a $C_{1-5}$ alkyl group or a hydrogen atom), —O—, —S—, —SO—, —SO$_2$— and any combinations thereof. The divalent linking group is preferably selected from the group consisting of an alkylene group, a phenylene group, —CO—, —NR$^a$—, —O—, —S—, —SO$_2$— and any combinations thereof. The number of carbon atom(s) in the alkylene group is preferably from 1 to 12. The number of carbon atoms in the alkenylene group is preferably from 2 to 12. The number of carbon atoms in the aryl group is preferably from 6 to 10.

(X2)

In the formula, R represents a substituent group; and m is an integer of from 0 to 5. When m is equal to or more than 2, two or more R are same or different from each other. Preferable examples of the substituent group represented by R are same as those exemplified above as an example of $R^1$, $R^2$ or $R^3$ in formula (X1). In the formula, m is preferably from 1 to 3, and is especially preferably 2 or 3.

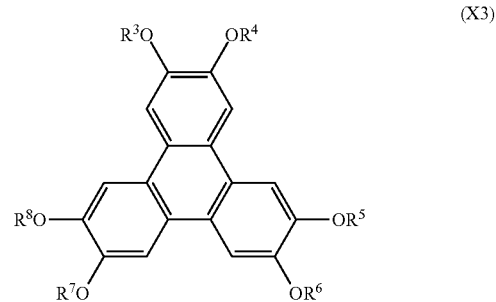

(X3)

In the formula, $R^4$, $R^5$, $R^6$, $R^7$, $R^6$ and $R^9$ each independently represent a hydrogen atom or a substituent group. Preferable examples of $R^4$, $R^5$, $R^6$, $R^7$, $R^8$ or $R^9$ include those exemplified above as an example of $R^1$, $R^2$ or $R^3$ in formula (X1).

Examples of the compound represented by formula (X1), (X2) or (X3), which can be used as an alignment controlling agent, include the compounds described in JPA 2005-99248.

One compound of formula (X1), (X2) or (X3) may be used alone, or two or more compounds of formula (X1), (X2) or (X3) may be used in combination.

An amount of the compound represented by formula (X1), (X2) or (X3) to be added to the liquid crystal composition is preferably from 0.01 to 10% by mass, more preferably from 0.01 to 5% by mass, or especially preferably from 0.02 to 1 by mass, with respect to an amount of the liquid crystal compound.

(5) Other Additives

The composition of the invention may contain one or two or more additives; and examples of the additive include antioxidants, UV absorbers, sensitizers, stabilizing agents, plasticizers, chain transfer agents, polymerization inhibitors, antifoamers, leveling agents, thickners, flame retarders, surfactants, dispersants, and colorants such as dyes and pigments.

(6) Process for Preparing Films of Composition

The composition of the invention is useful for preparing optical films such as retardation films and reflective films. One example of the process for preparing the film comprising (i) applying the polymerizable liquid crystal composition of the invention to the surface of a substrate or the like to form a liquid crystal phase (a cholesteric liquid crystal phase); and (ii) irradiating the curable liquid-crystal composition with ultraviolet light for promoting the curing reaction, thereby fixing the liquid crystal phase (the cholesteric liquid crystal phase) and then forming a light-reflective layer.

The steps of (i) and (ii) may be repeated to form a lamination of the plural cured films.

In the step (i), at the first, the polymerizable liquid crystal composition of the invention is applied to the surface of a substrate or an alignment layer formed thereon. The composition of the invention is preferably prepared as a coating liquid in which the ingredients are dissolved and/or dispersed in a solvent. Examples of the solvent include amides such as N,N-dimethylformamide, sulfoxides such as dimethylsulfoxide, heterocyclic compounds such as pyridine, hydrocarbons such as benzene and hexane; alkyl halide such as chloroform and dichloromethane; esters such as methyl acetate and butyl acetate; ketones such as acetone and methyl ethyl ketone; ethers such as tetrahydrofuran and 1,2-dimethoxyethane; and 1,4-butanediol acetate. Among these, alkyl halide and ketones are preferable.

The coating liquid may be applied to the substrate or the like, according to various methods of a wire bar coating method, an extrusion coating method, a direct gravure coating method, a reverse gravure coating method, a die coating method or the like. As the case may be, an inkjet apparatus may be used in which a liquid-crystal composition may be jetted out through a nozzle to form the intended coating film.

Next, the coating film of the liquid-crystal composition formed on the surface of the substrate or the like is made to have a liquid crystal phase such as a cholesteric liquid crystal phase. In an embodiment where the curable liquid-crystal composition is prepared as a coating liquid that contains a solvent, the coating film may be dried to remove the solvent, thereby the coating film may be made to have the intended liquid-crystal phase. If desired, the coating film may be heated up to the transition temperature to the cholesteric liquid-crystal phase. For example, the coating film is once heated up to the temperature of the isotropic phase, and then cooled to the liquid crystal phase transition temperature, whereby the film may stably have the intended liquid-crystal phase. The liquid-crystal transition temperature of the liquid crystal composition is preferably within a range of from 10 to 250 degrees Celsius from the viewpoint of the production aptitude, more preferably within a range of from 10 to 150 degrees Celsius. When the temperature is lower than 10 degrees Celsius, the coating film may require a cooling step or the like for cooling it to the temperature range within which the film could exhibit a liquid-crystal phase. On the other hand, when the temperature is higher than 250 degrees Celsius, the coating film may require a higher temperature in order that it could be in an isotropic liquid state at a higher temperature than the temperature range within which the film once exhibits a liquid-crystal phase; and this is disadvantageous from the viewpoint of heat energy dissipation, substrate deformation, degradation, etc.

Next, in the step (ii), the coating film in a liquid crystal state is irradiated with ultraviolet light to promote the curing reaction thereof. The curing reaction may be carried out according to a radical polymerization process, anionic polymerization process, cationic polymerization process, or coordination polymerization process. The type of the polymerization process may be selected depending on the compound represented by formula (I). The polymer, containing a unit derived from the compound represented by formula (I), is obtained in the polymerization process.

For ultraviolet irradiation, used is a light source of an ultraviolet lamp or the like. In this step, the ultraviolet irradiation promotes the curing reaction of the liquid-crystal composition, and the liquid crystal phase such as a cholesteric liquid crystal phase is thereby fixed and the intended light-reflective layer is thus formed.

The ultraviolet irradiation energy dose is not specifically defined, but in general, it is preferably from 100 mJ/cm$^2$ to 800 mJ/cm$^2$ or so. Not specifically defined, the time for ultraviolet radiation to the coating film may be determined from the viewpoint of both the sufficient strength of the cured film and the producibility thereof.

For promoting the curing reaction, ultraviolet irradiation may be attained under heat. The temperature in ultraviolet irradiation is preferably kept within a temperature range within which the cholesteric liquid-crystal phase can be kept safely as such with no disturbance. The oxygen concentration in the atmosphere participates in the degree of polymerization of the cured film. Accordingly, in case where the cured film could not have the intended degree of polymerization in air and the film strength is therefore insufficient, preferably, the oxygen concentration in the atmosphere is lowered according to a method of nitrogen purging or the like.

In the above step, the cholesteric liquid-crystal phase is fixed and the intended light-reflective layer is thereby formed. A most typical and preferred embodiment of the "fixed" liquid-crystal state is such that the alignment of the liquid-crystal compound to form the liquid crystal phase is held as such, to which, however, the invention is not limited. Concretely, the fixed state means that, in a temperature range of generally from 0 to 50 degrees Celsius, or from −30 to 70 degrees Celsius under a severer condition, the layer does not have flowability and does not undergo any alignment morphology change in an external field or by an external force applied thereto, and the layer can continue to stably keep the fixed alignment morphology. In the invention, the alignment state of the liquid-crystal phase is fixed through the curing reaction as promoted by ultraviolet irradiation.

In the invention, it is enough that the optical properties of the liquid crystal phase are held in the layer, and finally it is any more unnecessary that the liquid-crystal composition in the cured layer exhibits liquid crystallinity. For example, the liquid-crystal composition may be converted to a high-molecular weight substance and may lose the liquid crystallinity.

The thickness of the cured layer is not limited. The preferable thickness is determined depending on its application or the desired optical properties. Usually, the thickness is preferably from 0.05 to 50 micro meters, or more preferably from 1 to 35 micro meters.

(7) Substrate

The film of the invention may have a substrate. The substrate may be selected from those having a self-supporting property or those capable of supporting the cured layer. The materials or optical properties thereof are not limited. In some applications, the substrate may be required to have a high transmission for a visible light. Polymer films having a high transmission for a visible light include those used in display devices such as a liquid crystal display device as an optical film. Preferable examples of the polymer film which can be used as a substrate include poly ester films such as polyethylene terephthalate (PET), polybutylene and polyethylene naphthalate (PEN) films; polycarbonate (PC) films; polymethylmethacrylate films; polyolefin films such as polyethylene and polypropylene films; polyimide films, triacetyl cellulose (TAC) films. Polyethylene terephthalate and triacetyl cellulose are preferable.

(8) Alignment Layer

The film of the invention may have an alignment layer disposed between the cured layer and the substrate. The alignment layer may have a function capable of aligning liquid crystal molecules in the cholesteric liquid crystal layer more precisely. The alignment layer may be prepared by subjecting a film made of an organic compound (preferably a polymer) to a rubbing treatment, obliquely depositing an inorganic compound, forming a layer having microgrooves. Alignment layers having an alignment effect under an electric or magnetic field or irradiation are also known. Among these, alignment layers prepared by subjecting a film of a polymer to a rubbing treatment are preferred.

Examples of the material which can be used for preparing the alignment layer include polymers such as polymethylmethacrylate, acrylic acid/methacrylic acid copolymer, styrene/maleimide copolymer, polyvinyl alcohol, modified polyvinyl alcohol, poly(N-methylolacrylamide), styrene/vinyl toluene copolymer, chloridosulfuric polyethylene, cellulose nitrate, polyvinyl chloride, chlorinated polyolefin, polyester, polyimide, vinyl acetate/vinyl chloride copolymer, ethylene/vinyl acetate copolymer, carboxymethyl cellulose, gelatin, polyethylene, polypropylene and polycarbonate; and silane coupling agents. Preferable examples of the polymer are water-soluble polymers such as poly(N-methylolacrylamide), carboxymethyl cellulose, gelatin, polyvinyl alcohol and modified polyvinyl alcohol; gelatin, polyvinyl alcohol polarizing elements, selective reflection films, color filters, anti-reflection films, optical compensation films, holography, and alignment layers.

3. Polymer

The present invention relates to polymers prepared by carrying out polymerization of one or two or more polymerizable liquid crystal compounds represented by formula (I), to polymers prepared by carrying out polymerization of the polymerizable liquid crystal composition of the invention. The polymers may exhibit liquid-crystallinity or non-liquid-crystallinity. The polymers have the repeating unit derived from the polymerizable liquid crystal compound represented by formula (I), may exhibit high Δn, and may be useful as a material of various optical elements.

EXAMPLES

Paragraphs below will further specifically describe features of the present invention, referring to Examples and Comparative Examples. Any materials, amount of use, ratio, details of processing, procedures of processing and so forth shown in Examples may appropriately be modified without departing from the spirit of the present invention. Therefore, it is to be understood that the scope of the present invention should not be interpreted in a limited manner based on the specific examples shown below.

Example 1

Synthetic Example of Compound (I-1)

Compound (I-1) was prepared according to the following scheme.

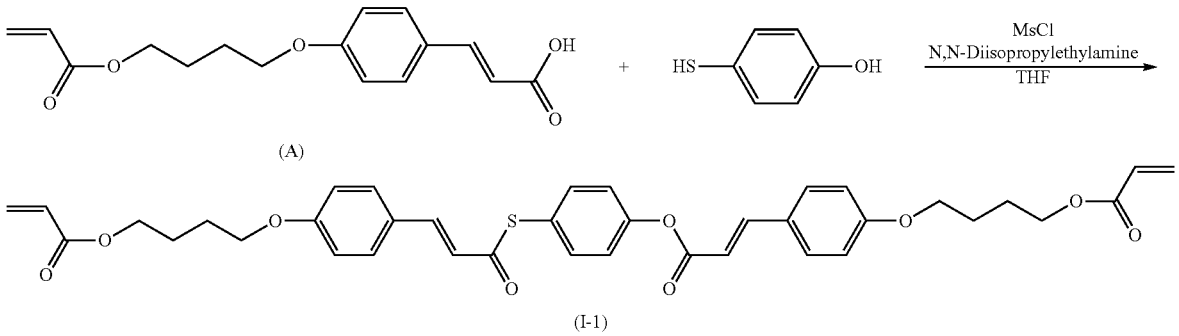

and modified polyvinyl alcohol are more preferable; and polyvinyl alcohol and modified polyvinyl alcohol are specially preferable.

(9) Applications of Films

One embodiment of the film of the invention is a film of the cured liquid crystal alignment (for example, horizontal alignment, vertical alignment, hybrid alignment) of the polymerizable liquid crystal composition, exhibiting optical anisotropy. The film may be used as an optical compensation film for liquid crystal displaying devices.

Another embodiment of the film of the invention is a film of the cured cholesteric liquid crystal phase of the polymerizable liquid crystal composition, exhibiting selective reflection at the wavelength range. The film exhibiting selective reflection at the IR wavelength region (800-1300 nm) may be attached to window plates of buildings or vehicles or may be incorporated into laminated glasses, which may be used as a heat-shielding member.

Or the film of the invention may be used in various technical fields of optical elements such as retardation plates, Synthesis of Intermediate (A):

Intermediate (A) was prepared according to the process described in Japanese Patent No. 4355406, p. 23, [0109]-[0110]. The determination of the obtained compound was performed by measurement of $^1$H-NMR spectra.

$^1$H-NMR (Solvent: CDCl$_3$, Standard: tetramethyl silane) δ (ppm): 1.85-1.95 (4 H, m), 4.03(2 H, t), 4.25(2 H, t), 5.82(1 H, d), 6.12(1 H, dd), 6.31(1H, d), 6.41(1 H, d), 6.91(2 H, d), 7.51(2 H, d), 7.73(1 H, d).

Synthesis of Compound (I-1):

Intermediate (A) (1.99 g) and tetrahydrofuran (THF) (10 mL) were put into a three-necked flask, and cooled to 0 degree Celsius by using a cooling medium of ice/methanol. After that, the mixture was added dropwise with mesylchloride (MsCl) (0.53 mL), and subsequently added with N,N-diisopropyl ethylamine (1.33 mL). After being stirred at 0 degree Celsius for 30 minutes, the mixture was added dropwise with 4-hydroxy thiophenol (0.42 g) and N,N-diisopropyl ethylamine (1.33 mL), and then stirred at a temperature for three hours. Methanol was poured into the obtained solution, and then condensed by a rotary evaporator. After that, the obtained concentrate was recrystallized in methanol to give 1.2 g of Compound (I-1) as a white solid (yield 54%). The determination of the obtained compound was performed by measurement of $^1$H-NMR spectra.

$^1$H-NMR (Solvent: CDCl$_3$, Standard: tetramethyl silane) δ (ppm): 1.85-1.95 (8 H, m), 4.01-4.10(4 H, m), 4.22-4.28(4 H, m), 5.82(2 H, d), 6.12(2 H, dd), 6.41(1 H, d), 6.49(1 H, d), 6.65(1 H, d), 6.82-6.95(6 H, m), 7.25(2 H, d), 7.46-7.63(4 H, m), 7.63(1 H, d), 7.82(1 H, d).

The texture of the obtained compound, Compound (I-1), was observed under a polarizing microscope while the temperature was increased, and the transition from the crystal phase to the nematic liquid crystal phase was observed at about 94 degrees Celsius, and the transition to the isotropic liquid phase was observed over 222 degrees Celsius. It was confirmed that Compound (I-1) exhibits a nematic liquid crystal phase in the temperature range of from 94 to 222 degrees Celsius.

Example 2

Synthetic Example of Compound (I-2)

Compound (I-2) was prepared according to the following scheme.

Intermediate (B) was prepared in the same manner as described in Japanese Patent No. 4355406. p. 23, [0109]-[0110], except that vanillin was used in place of 4-hydroxy benzaldehyde.

Synthesis of Compound (I-2):

Compound (I-2) was prepared in the same manner as Compound (I-1) by using Intermediates (A) and (B). The determination of the obtained compound was performed by measurement of $^1$H-NMR spectra.

$^1$H-NMR (Solvent: CDCl$_3$, Standard: tetramethyl silane) δ (ppm): 1.85-1.95 (4 H, m), 3.90(3 H s), 4.10(2 H, t), 4.25(2 H, t), 5.82(1 H, d), 6.12(1 H, dd), 6.31(1 H, d), 6.41(1 H, d), 6.91(2 H, d), 7.51(2 H, d), 7.73(1 H, d).

Example 3

Synthetic Example of Compound (I-3)

Compound (I-3) was prepared according to the following scheme in the same manner as Example 1, except that Intermediate (B) was used in place of Intermediate (A).

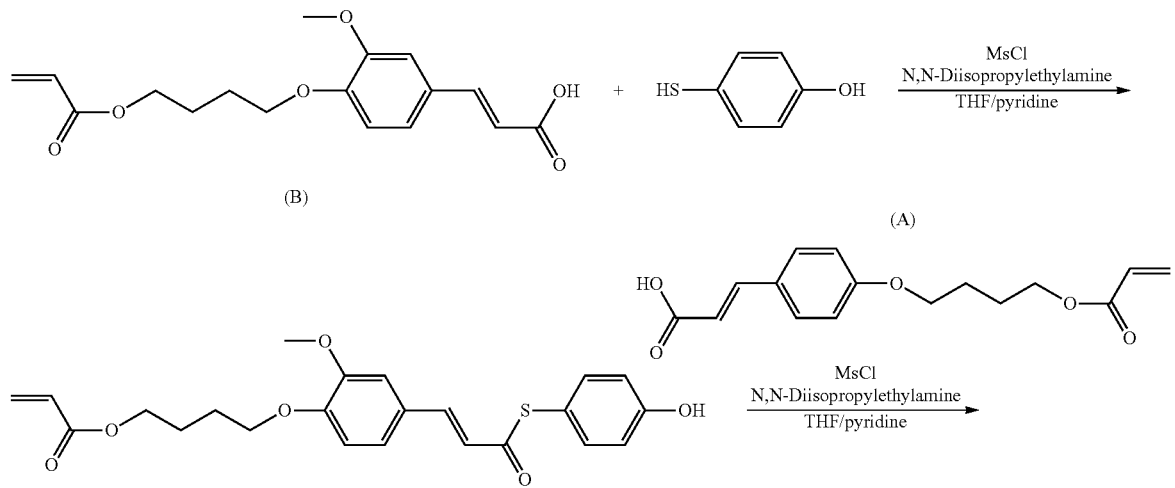

Synthesis of Intermediates (A) and (B):

Intermediate (A) was prepared in the same manner as described above.

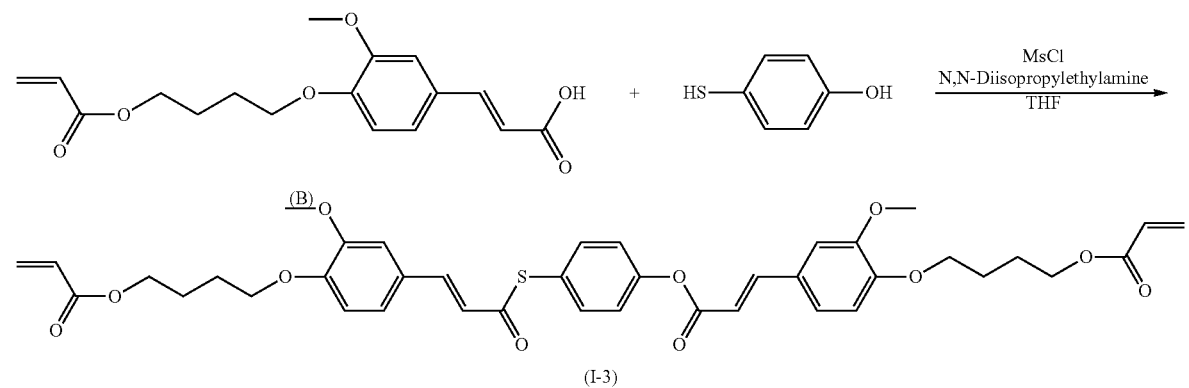

The determination of the obtained compound was performed by measurement of $^1$H-NMR spectra.

$^1$H-NMR (Solvent: CDCl$_3$, Standard: tetramethyl silane)δ (ppm): 1.85-1.95 (8 H, m), 3.90(6 H, s), 4.10(4 H, t), 4.25(4 H, t), 5.82(2 H, d), 6.12(2 H, dd), 6.31(2 H, d), 6.50(1 H, d), 6.91(2 H, d), 7.10-7.40(10 H, m), 7.58(2 H, d), 7.83(2 H, d), 8.11(1 H, d).

Example 4

Synthetic Example of Compound (II-3)

Compound (II-3) was prepared according to the following scheme.

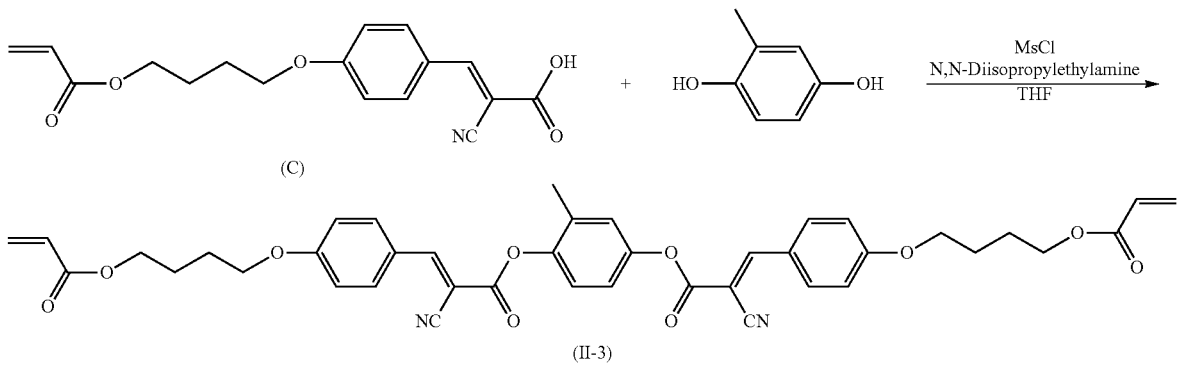

Synthesis of Intermediate (C):

Intermediate (C) was prepared in the same manner as the method described in Japanese Patent No. 4355406, p. 23, [0109]-[0110], except that cyano acetic acid was used in place

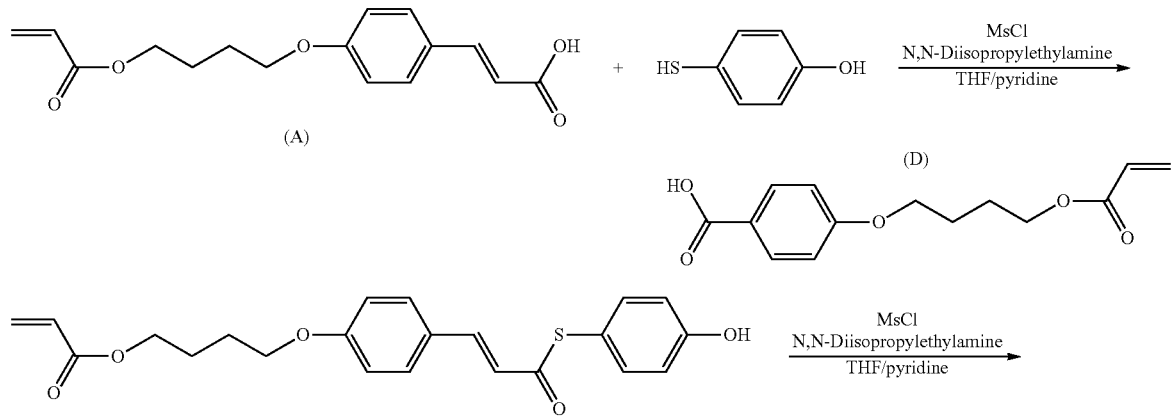

of malonic acid. The determination of the obtained compound was performed by measurement of $^1$H-NMR spectra.

$^1$H-NMR (400 MHz, CDCl$_3$):1.85-2.00(m, 4H), 4.10-4.15 (m, 2H), 4.25-4.30(m, 2H), 5.85(d, 1H), 6.15(dd, 1H), 6.40(d, 1H), 7.00(d, 2H), 8.00(d, 2H), 8.25(s, 1H).

Synthesis of Compound (II-3):

Compound (II-3) was prepared in the same manner as the process of preparing Compound (I-1), except that Intermediate (C) was used in place of Intermediate (A), and methyl hydroquinone was used in place of 4-hydroxy thiophenol.

The determination of the obtained compound was performed by measurement of $^1$H-NMR spectra.

$^1$H-NMR (Solvent: CDCl$_3$, Standard: tetramethyl silane)δ (ppm): 1.85-1.95 (8 H, m), 4.01-4.10(4 H, m), 4.22-4.28(4 H, m), 5.82(2 H, d), 6.12(2 H, dd), 6.41(2 H, d), 7.01(4 H, d), 7.11-7.28(4 H, m), 8.06(4 H, d), 8.31(1 H, s), 8.32(1 H, s).

Example 5

Synthesis of Compound (III-1)

Compound (III-1) was prepared according to the following scheme.

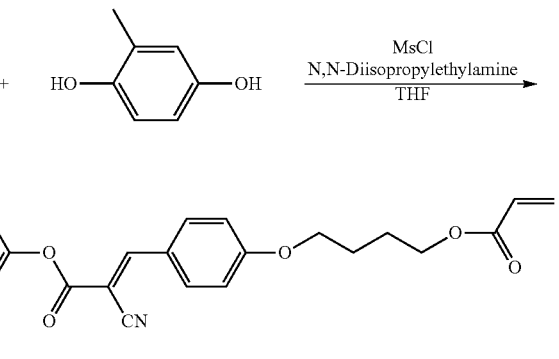

Synthesis of Intermediates (A) and (D):

Intermediate (A) was prepared in the same manner as described above.

Intermediate (D), 4-(4-acryloyloxy butyloxy)benzoic acid was prepared according to the process described in JP-A-2002-97170, p. 10, [0085]-[0087].

Synthesis of Compound (III-1):

0.8 g of Compound (III-1) was prepared in the same manner as the process of preparing Compound (I-1), except that Intermediates (A) and (D) were used. The determination of the obtained compound was performed by measurement of $^1$H-NMR spectra.

$^1$H-NMR (Solvent: CDCl$_3$, Standard: tetramethyl silane)δ (ppm): 1.85-1.95 (8 H, m), 4.00-4.11(4 H, m), 4.21-4.30(4 H, m), 5.82(2 H, d), 6.12(2 H, dd), 6.42(2 H, d), 6.67(1 H, d), 6.91(2 H, d), 6.98(2 H, d), 7.23-7.35(4 H, m), 7.50-7.58(4 H, m), 7.68(1 H, d), 8.16(2 H, d).

The texture of the obtained compound, Compound (III-1), was observed under a polarizing microscope while the temperature was increased, and the transition from the crystal phase to the nematic liquid crystal phase was observed at about 85 degrees Celsius, and the transition to the isotropic liquid phase was observed over 199 degrees Celsius. It was confirmed that Compound (III-1) exhibits a nematic liquid crystal phase in the temperature range of from 85 to 199 degrees Celsius.

[Properties of Compounds]

Δn of each of the compounds can be measured directly according to the method described in "Handbook of Liquid Crystal (Ekisho Binran)" (Ekisho Binran Editing Committee), p. 202. A wedge shape cell was filled with each of the compound prepared above, and was irradiated with a laser light having a wavelength of 532 nm. And the refracting angle of the transmitted light therefrom was measured, and on the basis of the data, Δn was calculated.

The Δn values of the compounds are shown in the following table. And the transition temperatures thereof are also shown in the following table.

The Δn values and the transition temperatures of Comparative Compounds (R-1) and (R-2) were obtained in the same manner as above respectively. And the results are also shown in the following table.

(R-1)

(R-2)

| Liquid crystalline compound | Transition Temperature (degrees Celsius) | Δn |
|---|---|---|
| Example 1 (I-1) | Cr 92 Ne 225 Iso | 0.334(60° C.) |
| Example 2 (I-2) | Cr 95 Ne 162 | 0.323(30° C.) |
| Example 3 (I-3) | Cr 118 (Ne 111) Iso | * |
| Example 4 (II-3) | Cr 124 Ne 139 Iso | * |
| Example 5 (III-1) | Cr 55 Ne 90 Iso | * |
| Comparative Example 1 (R-1) | Cr 73 Ne 180 Iso | 0.271(70° C.) |
| Comparative Example 2 (R-2) | Cr 80 Ne 124 Iso | 0.187(30° C.) |

*: The data was not available because of crystallization.

Example 6

Preparation of Retardation Film

A liquid crystal composition having the following formulation was prepared by using Compound (I-1), which was prepared in the above-described example. This was used as Coating Liquid (1).

| | |
|---|---|
| Compound (R-2) | 33 parts by mass |
| Polymerizable liquid crystal compound (1) | 67 parts by mass |
| Agent for controlling alignment at an air-interface (1) | 0.1 part by mass |
| Polymerization initiator IRGACURE819 (Ciba-Japan) | 3 parts by mass |
| Solvent chloroform | 800 parts by mass |

Polymerizable liquid crystal compound (1)

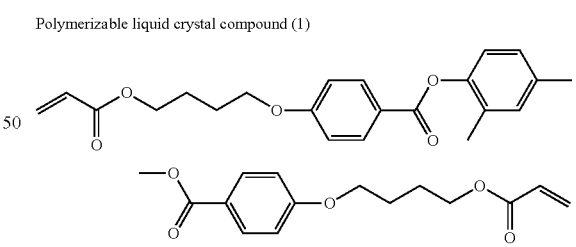

Agent for controlling alignment at an air-interface (1)

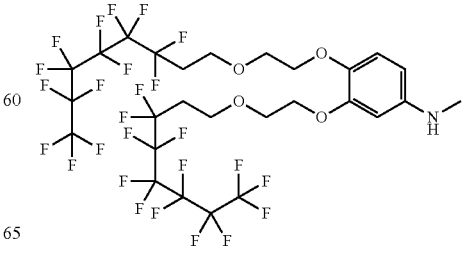

-continued

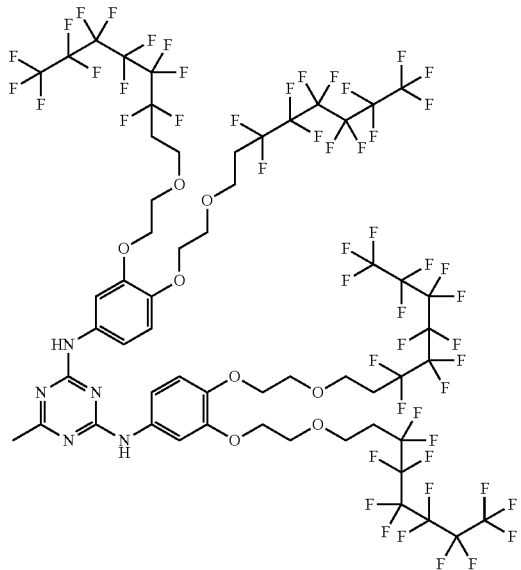

A glass substrate was washed and dried, a commercially-available polyimide alignment film (SE-130, from Nissan Chemical Industries, Ltd.) was formed according to a coating method using a wire bar, the coated film was heated at 250 degrees Celsius for one hour, allowed to cool, and rubbed at room temperature. Coating liquid (1) was applied to the surface of the alignment film according to a spin coating method at a room temperature. The coated film was heated at 120 degrees Celsius for 30 minutes for maturation, and then irradiated with UV light under an atmosphere of nitrogen gas at a room temperature for 10 seconds by a high-pressure mercury lamp without shorter wavelength components, thereby to fix the alignment and form a retardation film, Retardation film 1. During the period from the step of applying the coating liquid to the step of heating it, any precipitated crystals were not found.

Retardation film 1 was observed under a polarizing microscope, and the monoaxial alignment without any alignment defect was found in the film.

The film was measured in a Tip-Tilt mode by using AxoScan manufactured by AXOMETRIX. The averaged tilt angle calculated by AxoScan was 1 degree, and it was confirmed that an A-plate type retardation film was obtained.

The value of $\Delta n$ at a wavelength of 550 nm was 0.235, which was calculated on the basis of retardation, measured by AxoScan, and the thickness of the retardation film, measured by a confocal scanning laser thickness-measuring equipment, "FV-750", manufactured by KEYENCE. The haze value of the film was measured by using a Haze meter "NHD2000" (NIPPON DENSHOKU INDUSTREIS CO., LTD.), and it was found that the haze value of the film was 0.09.

Examples 7-10

Preparation of Retardation Films

Each of Liquid crystal compositions, Coating liquids (2)-(5), was prepared in the same manner as Example 6, except that each of the compounds prepared in the above examples was used in place of Compound (I-1). Each of Retardation films 2-5 was prepared in the same manner as Example 6.

All of the obtained retardation films showed a good alignment-property, and had a haze value of 0.1 or lower. The $\Delta n$ values at 550 nm of the retardation films, which were calculated in the same manner as described above, are shown in the following table.

Comparative Example 3

Formation of Comparative Retardation Film

A liquid crystal composition, having the following formulation, Coating liquid (11), was prepared in the same manner as Example 6.

| | |
|---|---|
| Polymerizable liquid crystal compound (R-2) | 100 parts by mass |
| Agent for controlling alignment at an air-interface (1) | 0.1 part by mass |
| Polymerization initiator IRGACURE819 (Ciba-Japan) | 3 parts by mass |
| Solvent chloroform | 800 parts by mass |

Retardation film 6 was prepared in the same manner as Example 6, except that Coating liquid (11) was used in place of Coating liquid (1). And the upper limit of the temperature at which the liquid crystal composition of Coating liquid (11) showed the liquid crystal phase was lower than that of Example 1, the maturing temperature was changed to 90 degrees Celsius. During the period from the step of applying the coating liquid to the step of heating it, some precipitated crystals were found. As a result, after maturing the alignment by heating again, unevenness in the thickness remained at the part of precipitation.

The $\Delta n$ value at 550 nm of Retardation film 6 of Comparative Example 3, which was calculated in the same manner as described above, was 0.170. The haze value of the film was 0.19.

Comparative Example 4

Formation of Comparative Retardation Film

A coating liquid of the liquid crystal composition was prepared in the same manner as Comparative Example 3, except that Polymerizable Liquid Crystal Compound (R-1) was used in place of Polymerizable Liquid Crystal Compound (R-2). A retardation film was prepared in the same manner as Comparative Example 3, except that the coating liquid was used.

The $\Delta n$ value at 550 nm of the retardation film, which was calculated in the same manner as described above, was 0.197. The haze value of the film was 0.1.

The results are shown in the following table.

TABLE 2

| Liquid Crystal Composition | Compound | $\Delta n$ | Haze |
|---|---|---|---|
| Example 6 | I-1 | 0.235 | 0.09 |
| Example 7 | I-2 | 0.216 | 0.07 |
| Example 8 | I-3 | 0.218 | 0.07 |
| Example 9 | II-3 | 0.201 | 0.08 |
| Example 10 | III-1 | 0.206 | 0.09 |
| Comparative Example 3 | R-2 | 0.170 | 0.19 |
| Comparative Example 4 | R-1 | 0.197 | 0.10 |

From the data shown in the above table, it is understandable that the compounds represented by formula (I) have higher Δn, compared with the known liquid crystal compounds.

Example 11

Formation of Selective Reflection Film

A liquid crystal composition having the following formulation was prepared by using Compound (I-1), which was prepared in the above-described example. This was used as Coating Liquid (6).

| | |
|---|---|
| Compound (I-1) | 33 parts by mass |
| Polymerizable liquid crystal compound (R-2) | 67 parts by mass |
| Chiral agent Paliocolor LC756 (BASF) | 3 parts by mass |
| Agent for controlling alignment at an air-interface (1) | 0.04 part by mass |
| Polymerization initiator IRGACURE819 (Ciba-Japan) | 3 parts by mass |
| Solvent chloroform | 300 parts by mass |

A substrate having an alignment layer thereon was prepared in the same manner as Example 6, and Coating liquid (6) was applied to the surface of the alignment layer at a room temperature according to a spin-coating method, heated at 120 degrees Celsius for three minutes for maturation, and then irradiated with UV light for 10 seconds at a room temperature by a high-pressure mercury lamp without shorter wavelength components, thereby to fix the alignment and form a selective reflection film, Selective reflection film 1. During the period from the step of applying the coating liquid to the step of heating it, any precipitated crystals were not found.

Selective reflection film 1 was observed under a polarizing microscope, and the uniform alignment without any alignment defect was found in the film. The transmission spectrum of the film was measured by using spectral photometer "UV-3100PC" (Shimadzu Corporation), and it was found that the film had a peak of selective reflection at 1000 nm of which half bandwidth was 147 nm. The Δn of the film which was calculated on the basis of the half bandwidth of the peak and the helical pitch of the liquid crystal composition was 0.22. The haze value of the film was measured by using a Haze meter "NHD2000" (NIPPON DENSHOKU INDUSTREIS CO., LTD.), and it was found that the haze value of the film was 0.09.

Examples 12-15

Formation of Selective reflection Films

Liquid crystal compositions, Coating liquids (7)-(10), were prepared in the same manner as Example 11, except that the compounds prepared in Examples were respectively used in place of Compound (I-1). Selective reflection films 2-5 were respectively prepared in the same manner as Example 11, except that each of Coating liquids (7)-(10) was used in place of Coating liquid (6). All of the obtained selective reflection films showed a good alignment-property, and had a haze value of 0.15 or lower. The Δn value and the half bandwidth of the peak of each of the films are shown in Table 3.

Comparative Example 5

Formation of Selective Reflection Film for Comparative Example (Formation of Selective Reflection Film)
A liquid crystal composition, Coating liquid (12), having the following formulation was prepared in the same manner as Example 11.

| | |
|---|---|
| Polymerizable liquid crystal compound (R-2) | 100 parts by mass |
| Chiral agent Paliocolor LC756 (BASF) | 2.8 parts by mass |
| Agent for controlling alignment at an air-interface (1) | 0.04 part by mass |
| Polymerization Initiator IRGACURE819 (Ciba-Japan) | 3 parts by mass |
| Solvent Chloroform | 300 parts by mass |

A selective reflection film was prepared in the same manner as Example 6, except that Coating liquid (12) was used in place of Coating liquid (6). And the upper limit of the temperature at which the liquid crystal composition of Coating liquid (12) showed the liquid crystal phase was lower than that of Example 6, the maturing temperature was changed to 90 degrees Celsius.

During the period from the step of applying the coating liquid to the step of heating it, some precipitated crystals were found. As a result, after maturing the alignment by heating again, unevenness in the thickness remained at the part of precipitation.

The film had a peak of selective reflection at 1000 nm of which half bandwidth was 106 nm. The Δn of the film which was calculated on the basis of the half bandwidth of the peak and the helical pitch of the liquid crystal composition was 0.170. The haze value of the film was measured by using a Haze meter "NHD2000" (NIPPON DENSHOKU INDUSTREIS CO., LTD.), and it was found that the haze value of the film was 0.65.

Comparative Example 6

Formation of Selective Reflection Film for Comparative Example

A coating liquid of the liquid crystal composition was prepared in the same manner as Comparative Example 5, except that Polymerizable liquid crystal compound (R-1) was used in place of Polymerizable liquid crystal compound (R-2): and a selective reflection film was prepared in the same manner as Comparative Example 5, except that the coating liquid was used.

The film had a peak of selective reflection at 1000 nm of which half bandwidth was 127 nm. The Δn of the film which was calculated on the basis of the half bandwidth of the peak and the helical pitch of the liquid crystal composition was 0.199. The haze value of the film was measured by using a Haze meter "NHD2000" (NIPPON DENSHOKU INDUSTREIS CO., LTD.), and it was found that the haze value of the film was 0.08.

The results are shown in the following table.

TABLE 3

| Liquid Crystal Composition | Compound | Half bandwidth | Δn | Haze |
|---|---|---|---|---|
| Example 11 | I-1 | 147 nm | 0.232 | 0.09 |
| Example 12 | I-2 | 136 nm | 0.215 | 0.07 |
| Example 13 | I-3 | 136 nm | 0.215 | 0.07 |
| Example 14 | II-3 | 128 nm | 0.202 | 0.08 |

TABLE 3-continued

| Liquid Crystal Composition | Compound | Half bandwidth | Δn | Haze |
|---|---|---|---|---|
| Example 15 | III-1 | 130 nm | 0.205 | 0.09 |
| Comparative Example 5 | R-2 | 106 nm | 0.168 | 0.65 |
| Comparative Example 6 | R-1 | 127 nm | 0.199 | 0.08 |

From the data shown in the above table, it is understandable that the compounds represented by formula (I) have higher Δn, compared with the known liquid crystal compounds.

What is claimed is:

1. A compound represented by formula (I):

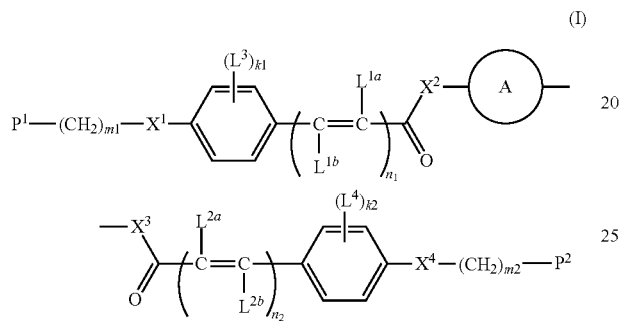

where
P$^1$ and P$^2$ each independently represent a polymerizable group;
m1 and m2 each independently represent an integer of from 1 to 10, and one CH$_2$ or two or more CH$_2$, which may be not adjacent to each other, in —(CH$_2$)$_{m1}$— and —(CH$_2$)$_{m2}$— may be replaced with —O— or —S—;
"A" represents a divalent group having a 5- to 18-membered aromatic hydrocarbon ring or a 5- to 18-membered aromatic hetero ring, in which at least one hydrogen atom may be replaced with a C$_{1-4}$ alkyl group, C$_{1-4}$ alkoxy group or halogen atom;
L$^3$ and L$^4$ each independently represent a C$_{1-10}$ alkyl group or a C$_{1-10}$ alkoxy group, k1 and k2 each independently represent an integer of from 0 to 4;
X$^1$, X$^2$, X$^3$ and X$^4$ each independently represent —O—, —S—, —NH—, —NR— or —SiR$^o$R$^{oo}$—, R, R$^o$ and R$^{oo}$ each independently represent a C$_{1-10}$ alkyl group;
n1 and n2 each independently represent 0 or 1, provided that at least one of them is 1; and
L$^{1a}$, L$^{1b}$, L$^{2a}$ and L$^{2b}$ each independently represent a hydrogen atom, halogen atom, —CN, —NC, —NCO, —NCS, or —OCN,
provided that those in which both of X$^2$ and X$^3$ represent —O—, those in which one of X$^2$ and X$^3$ represents —O— and another represents —NH— or —NR— are excluded only when n1 is 1, both of L$^{1a}$ and L$^{1b}$ are hydrogen atoms, n2 is 1, and both of L$^{2a}$ and L$^{2b}$ are hydrogen atoms, or only when n1 is 1, both of L$^{1a}$ and L$^{1b}$ are hydrogen atoms, and n2 is 0.

2. The compound of claim 1, wherein "A" is a divalent group having a 6-membered aromatic hydrocarbon ring.

3. The compound of claim 2, wherein at least one of X$^2$ and X$^3$ represents —S—.

4. The compound of claim 1, wherein P$^1$ and P$^2$ each independently represent a polymerizable group selected from the group consisting of the groups represented by (P-1)-(P-5) shown below:

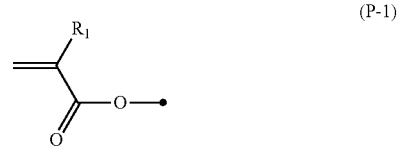

where R$^1$ to R$^3$ each independently represent a hydrogen atom or methyl.

5. The compound of claim 1, wherein P$^1$ and P$^2$ each independently represent a methacrylate or acrylate group.

6. A polymerizable liquid crystal composition comprising at least one compound of claim 1.

7. The polymerizable liquid crystal composition of claim 6, comprising at least one chiral compound.

8. A polymer prepared by polymerizing a compound of claim 1.

9. A polymer prepared by polymerizing a polymerizable liquid crystal composition of claim 6.

10. A film comprising at least one polymer of claim 8.

11. A film formed by curing a cholesteric liquid crystal phase of a polymerizable liquid crystal composition of claim 7.

12. The film of claim 10, having optical anisotropy.

13. The film of claim 10, having selective reflection.

14. The film of claim 10, having selective reflection in the infrared region.

* * * * *